United States Patent
Hanson et al.

(10) Patent No.: US 7,851,620 B2
(45) Date of Patent: Dec. 14, 2010

(54) METHODS FOR PREPARING DIAZONAMIDES

(75) Inventors: Gunnar Hanson, Chapel Hill, NC (US); Charles Caldwell, Dallas, TX (US); Patrick G. Harran, Los Angeles, CA (US); Susan Harran, Dallas, TX (US); Qi Wei, Dallas, TX (US); Ming Zhou, Coppell, TX (US)

(73) Assignees: Board of Regents, The University of Texas System, Austin, TX (US); Joyant Pharmaceuticals, Inc., Dallas, TX (US)

( * ) Notice: Subject to any disclaimer, the term of this patent is extended or adjusted under 35 U.S.C. 154(b) by 217 days.

(21) Appl. No.: 12/134,984

(22) Filed: Jun. 6, 2008

(65) Prior Publication Data
US 2009/0005572 A1    Jan. 1, 2009

Related U.S. Application Data

(60) Provisional application No. 60/933,916, filed on Jun. 7, 2007, provisional application No. 60/954,275, filed on Aug. 6, 2007.

(51) Int. Cl.
*C07D 498/22* (2006.01)
*C07D 263/00* (2006.01)
*C07D 263/34* (2006.01)

(52) U.S. Cl. ................ 540/456; 548/236; 548/218
(58) Field of Classification Search ............. 540/456; 548/236, 218
See application file for complete search history.

(56) References Cited

U.S. PATENT DOCUMENTS

| 6,872,721 | B2 | 3/2005 | Orme et al. |
| 7,022,720 | B2 | 4/2006 | Harran et al. |
| 2005/0227955 | A1 | 10/2005 | Adams et al. |
| 2005/0282805 | A1 | 12/2005 | Hangeland et al. |
| 2006/0089397 | A1 | 4/2006 | Harran et al. |
| 2007/0149583 | A1 | 6/2007 | Harran et al. |

FOREIGN PATENT DOCUMENTS

WO    WO-03/106438    12/2003

OTHER PUBLICATIONS

Burgett et al. Angew. Chem. Int. Ed. 2003, 42, 4961-4966.*
Konda-Yamada et al., Tetrahedron (2002) 58:7851-7861.
Patani et al., Chem Rev (1996) 96:3147-3176.
Yokoyama et al., Eur J Org Chem (2004) 1244-1253.
Yokoyama et al., Tetrahedron Letters (1999) 40:7803-7806.
International Search Report and Written Opinion for PCT/US08/66204, mailed Sep. 11, 2008, 8 pages.
Nicolaou et al., J. Am. Chem. Soc. (2004) 126:12888-12896.

* cited by examiner

*Primary Examiner*—Rebecca L Anderson
*Assistant Examiner*—Jason M Nolan
(74) *Attorney, Agent, or Firm*—Richard Aron Osman

(57) ABSTRACT

This invention relates to novel macrocyclic lactams intermediates useful for the preparation of diazonamide analogs. This invention also relates to a novel electrochemical oxidative cyclization for the preparation of such macrocyclic lactams, and their further elucidation to provide diazonamide analogs.

22 Claims, 3 Drawing Sheets

METHODS FOR PREPARING DIAZONAMIDES

RELATED APPLICATIONS

This application claims benefit of priority to U.S. Provisional Application Ser. No. 60/933,916 filed 7 Jun. 2007; and U.S. Provisional Application Ser. No. 60/954,275 filed 6 Aug. 2007. The contents of these documents are incorporated herein by reference in their entirety.

STATEMENT OF RIGHTS TO INVENTIONS MADE UNDER FEDERALLY SPONSORED RESEARCH

This invention was made with grant support from the National Institutes of Health (2R01GM060591). The United States government has certain rights in this invention.

TECHNICAL FIELD

This invention relates to novel macrocyclic lactam intermediates useful for the preparation of diazonamide analogs. This invention also relates to novel methods for the preparation of such macrocyclic intermediates, and their further elucidation to provide diazonamide analogs.

BACKGROUND ART

Diazonamide A is a mitotic spindle-disrupting agent first isolated from the marine organism *Diazona angulata*, having the structure:

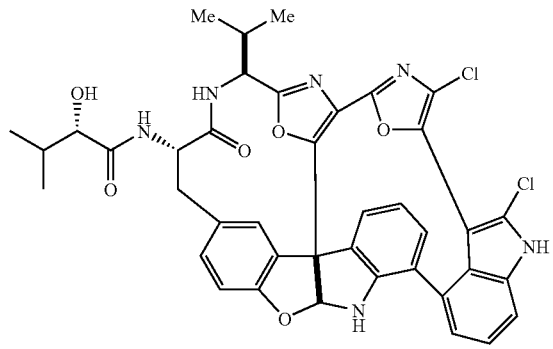

Numerous attempts have been made to synthesize this compound and its analogs. PCT publication WO 03/106438 describes a putative synthetic route; however, the structure identified as diazonamide A provided in that publication is incorrect. U.S. Pat. No. 7,022,720 correctly discloses the structure of diazonamide A and describes the synthesis of some of its analogs through the combined use of catalytic Heck endocyclization, stereo-controlled ring-contracting Pinacol rearrangement, and indole arylation via internal photo-induced electron transfer. Generic structures of some analogs are provided. U.S. Ser. No. 11/264,502 was filed 31 Oct. 2005 as a continuation-in-part of U.S. Ser. No. 10/227,509 (now U.S. Pat. No. 7,022,720), and is published as US 2006/0089397. U.S. Ser. No. 11/591,016 was filed 31 Oct. 2006 as a continuation-in-part of U.S. Ser. No. 11/264,502 (pending), and is published as US 2007/0149583.

In spite of considerable synthetic efforts, there is still a need to discover improved, more efficient processes and novel intermediates for use in the synthesis of diazonamide analogs.

DISCLOSURE OF THE INVENTION

Figure 1:
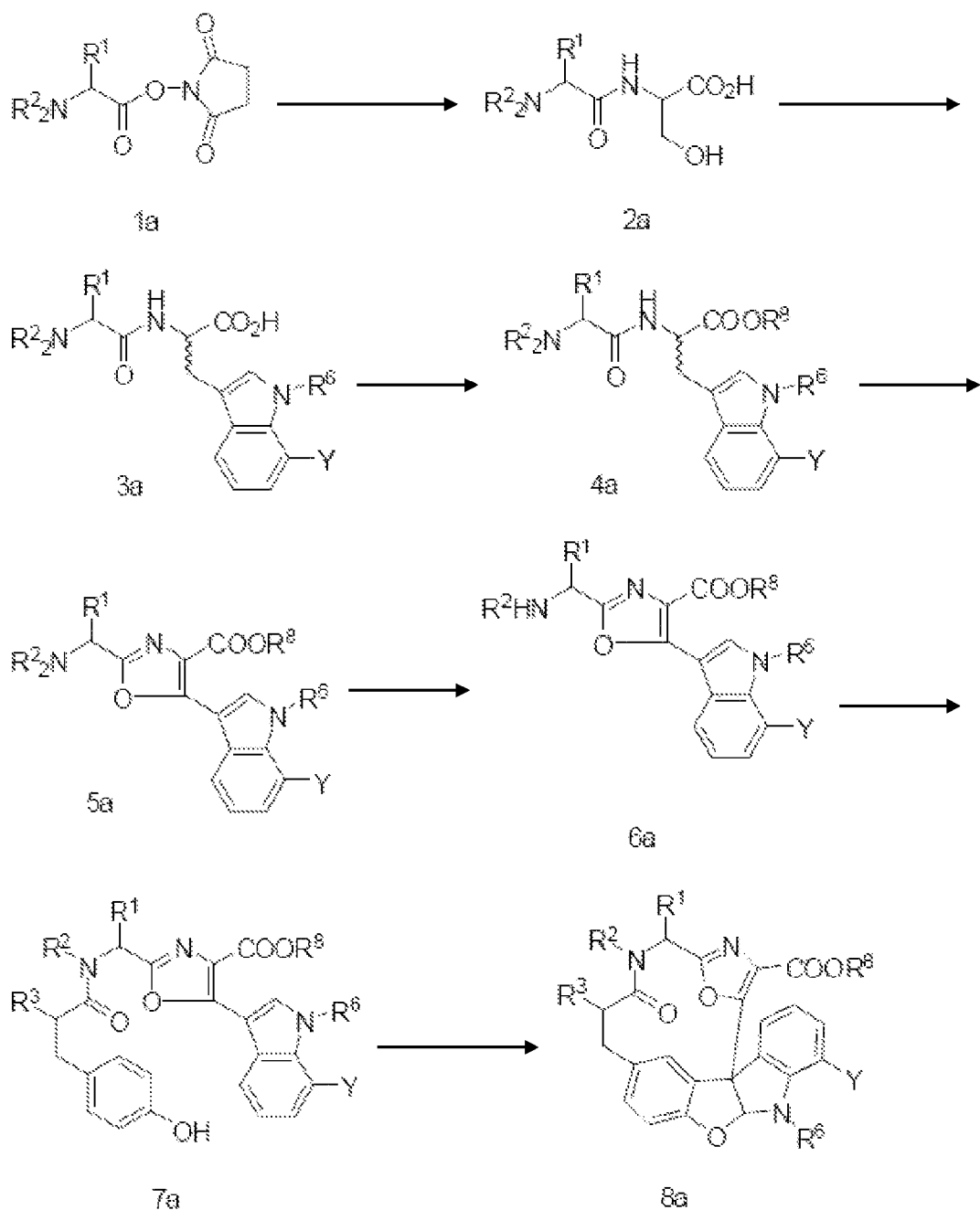
FIG. 1 shows a general synthetic route for the preparation of macrocyclic lactams of formula (I).

This invention relates to an efficient process for the preparation of novel macrocyclic lactams. These macrocyclic lactams are key intermediates in the synthesis of diazonamide analogs, which are anti-mitotic compounds useful as antiproliferative and anti-cancer agents, in particular for the treatment of paclitaxel-resistant cancers.

The macrocyclic lactams of the present invention are useful as intermediates for the preparation of diazonamide analogs. In particular, these macrolactams may be further elucidated to form diazonamide analogs, as disclosed herein.

As the stereochemistry of diazonamide analogs may affect their pharmaceutical activity, it is desirable to employ intermediates which will provide the final diazonamide products with the stereochemistry sought. The methods of the present invention provide a stereo-controlled route to macrocyclic lactams, which are useful intermediates for the preparation of diazonamide analogs.

The methods of the present invention are further advantageous in terms of the yield and purity of the macrocyclic lactam intermediates and the final diazonamide analogs produced therefrom. In particular, the methods of the present invention allow efficient conversion, and therefore the use of lesser amounts of starting materials, as well as simplified separation and purification procedures, for the preparation of these macrocyclic lactams and diazonamide analogs.

The present invention also provides methods for using the aforementioned macrocyclic lactams of formula (I) for the preparation of diazonamide analogs, and the novel diazonamide analogs prepared therefrom.

In one aspect, the invention provides a compound of formula (I):

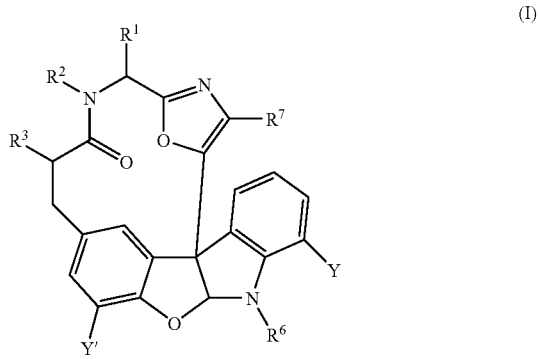

or a salt thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; or $R^1$ and $R^2$ may be taken together with the atoms to which they are attached to form a 5- or 6-member ring containing one nitrogen atom;

$R^3$ is H, or —$NR^4R^5$;

$R^4$ is H, or C1-C4 alkyl;

$R^5$ is H, or C1-C8 alkyl, C1-C8 heteroalkyl, C6-C14 arylalkyl, C6-C14 heteroarylalkyl, arylsulfonyl, trialkylsilyl, or alkoxycarbonyl, each of which may be optionally substituted; or —C(=X)R' where X is O, S, or NH, and R' is optionally fluorinated C1-C8 alkyl, C2-C8 alkenyl, C5-C12 aryl, or C6-C14 arylalkyl, each of which may be optionally substituted; or $R^4$ and $R^5$ may be taken together with nitrogen to form an imine, or an optionally substituted 3-8 membered monocyclic azacyclic ring or 8-12 membered bicyclic fused azacyclic ring, each of which may contain 0-2 additional heteroatoms selected from N, O, and S as ring members;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

$R^7$ is H, or halo, —CN, optionally substituted C1-C6 acyl, —$COOR^8$, or —$C(O)NR^9{}_2$;

$R^8$ is H, or C1-C8 alkyl, C2-C8 alkenyl, C5-C6 aryl, C6-C14 arylalkyl, or trialkylsilyl; and each $R^9$ is independently H, or C1-C8 alkyl, C2-C8 alkenyl, C5-C6 aryl, C6-C14 arylalkyl, C6-C14 heteroarylalkyl, —OH, or C1-C4 alkoxy, each of which may be optionally substituted; or two $R^9$ on the same N can optionally cyclize to form a ring; and each of Y and Y' is independently H, or halo, —OH, or —$OR^{10}$, where $R^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted.

In another aspect, the invention provides a method for the preparation of a compound of formula (I):

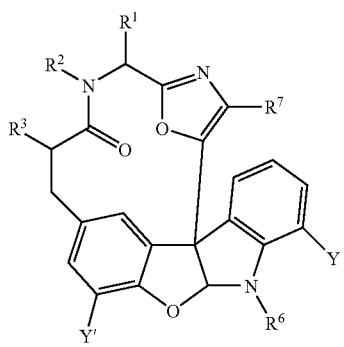

(I)

or a salt thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; or $R^1$ and $R^2$ may be taken together with the atoms to which they are attached to form a 5- or 6-member ring containing one nitrogen atom;

$R^3$ is H, or —$NR^4R^5$;

$R^4$ is H, or C1-C4 alkyl;

$R^5$ is H, or C1-C8 alkyl, C1-C8 heteroalkyl, C6-C14 arylalkyl, C6-C14 heteroarylalkyl, arylsulfonyl, trialkylsilyl, or alkoxycarbonyl, each of which may be optionally substituted; or —C(=X)R' where X is O, S, or NH, and R' is optionally fluorinated C1-C8 alkyl, C2-C8 alkenyl, C5-C12 aryl, or C6-C14 arylalkyl, each of which may be optionally substituted; or $R^4$ and $R^5$ may be taken together with nitrogen to form an imine, or an optionally substituted 3-8 membered monocyclic azacyclic ring or 8-12 membered bicyclic fused azacyclic ring, each of which may contain 0-2 additional heteroatoms selected from N, O, and S as ring members;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

$R^7$ is H, or halo, —CN, optionally substituted C1-C6 acyl, —$COOR^8$, or —$C(O)NR^9{}_2$;

$R^8$ is H, or C1-C8 alkyl, C2-C8 alkenyl, C5-C6 aryl, C6-C14 arylalkyl, or trialkylsilyl; and each $R^9$ is independently H, or C1-C8 alkyl, C2-C8 alkenyl, C5-C6 aryl, C6-C14 arylalkyl, C6-C14 heteroarylalkyl, —OH, or C1-C4 alkoxy, each of which may be optionally substituted; or two $R^9$ on the same N can optionally cyclize to form a ring; and each of Y and Y' is independently H, or halo, —OH, or —$OR^{10}$, where $R^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted;

said method comprising electrochemical oxidation of a compound of formula (II):

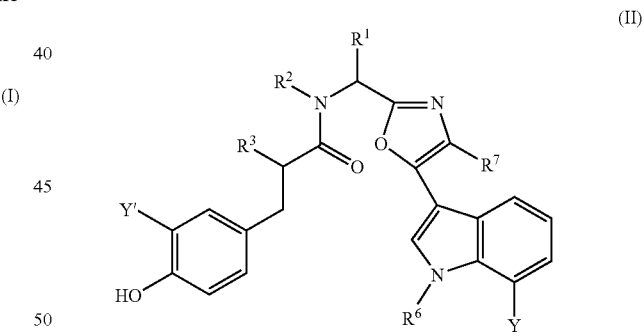

(II)

in which the radicals $R^1$, $R^2$, $R^3$, $R^6$, $R^7$, Y, and Y' are as defined for formula (I).

In certain embodiments, the method for preparation of a compound of formula (I) comprises an optional purification step, wherein the compound of formula (I) is purified chromatographically, by recrystallization, or by trituration, or by a combination of methods. In preferred embodiments, the compound of formula (I) is purified by trituration with methyl t-butyl ether (MTBE).

In other embodiments, the method for preparation of a compound of formula (I) comprises an additional step for removing any protecting groups that are present at $R^2$, $R^3$, $R^6$ or $R^7$.

In another aspect, the invention provides a method for the preparation of a compound of formula (3a):

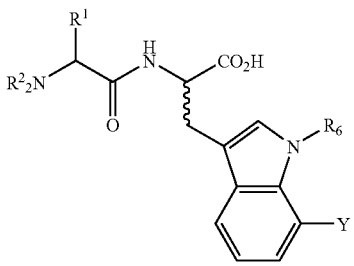

(3a)

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

each $R^2$ is independently H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; and Y is H, or halo, —OH, or —OR$^{10}$, where $R^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted;

said method comprising the steps of:

(a) contacting a compound of formula (2a):

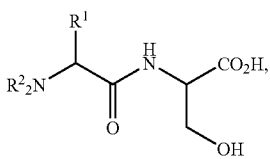

(2a)

with an indole of the formula:

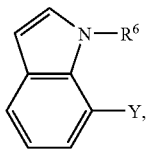

optionally in the presence of a protic acid, to provide a mixture;

wherein $R^1$, $R^2$, $R^6$, and Y are as defined for formula (3a);

(b) adding an activating reagent to said mixture; and (c) optionally heating said mixture to provide the compound of formula (3a).

In a preferred embodiment, the activating agent is acetic anhydride, and the reaction is conducted in acetic acid at about 80° C.

MODES OF CARRYING OUT THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular forms "a", "an", and "the" include plural references unless indicated otherwise.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isopropyl, isobutyl, tert-butyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10 C or as C1-C10 or as C1-10 or as C1-10. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10 C (alkyl) or 2-10 C (alkenyl or alkynyl). Preferably they contain 1-8 C (alkyl) or 2-8 C (alkenyl or alkynyl). Sometimes they contain 1-4 C (alkyl) or 2-4 C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present. Exemplary heteroalkyls include alkoxyls such as O-alkyl, alkyl ethers, secondary and tertiary alkyl amines, alkyl sulfides, and the like.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than three contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a saturated or partially saturated, monocyclic or fused or spiro polycyclic, carbocycle that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or cycloalkylalkyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl. Also included within the definition of heteroacyl groups are thioacyl substituents, e.g., —C(=S)R, and imine groups, e.g., —C(=NH)R.

Acyl and heteroacyl groups are bonded to any group or molecule to which they are attached through the open valence of the carbonyl carbon atom. Typically, they are C1-C8 acyl groups, which include formyl, acetyl, trifluoroacetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. Preferably the monocyclic aryl and heteroaryl groups contain 5-6 ring members, and the bicyclic aryl and heteroaryl groups contain 8-10 ring members.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moieties.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl. Preferably, an arylalkyl group includes one or two optionally substituted phenyl rings and a C1-C4 alkylene that is unsubstituted or is substituted with one or two C1-C4 alkyl groups or C1-C4 heteroalkyl groups, where the alkyl or heteroalkyl groups can optionally cyclize to form a ring such as cyclopropane, dioxolane, or oxacyclopentane, and wherein the alkyl or heteroalkyl groups may be optionally fluorinated. Examples of arylalkyl groups include optionally substituted benzyl, phenylethyl, diphenylmethyl, and triphenylmethyl groups. Optional substituents when present on the aryl ring of an arylalkyl group are the same as those described herein for an aryl ring.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. For example, heteroaryl groups include pyridylmethyl, pyridylethyl, —O-benzyl, and the like.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)— and —C(Me)$_2$— may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$— would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

Unless otherwise indicated, the term "oxo" refers to =O.

"Halo", as used herein, includes fluoro, chloro, bromo and iodo. Fluoro, chloro, and bromo are often preferred.

"Amino" as used herein refers to $NH_2$, but where an amino is described as "substituted" or "optionally substituted", the term includes $NR_2$ wherein each R is independently H, or is an alkyl, alkenyl, alkynyl, acyl, aryl, or arylalkyl group or a heteroform of one of these groups, each of which may be optionally substituted with the substituents described herein as suitable for the corresponding type of group. The term also includes forms wherein the two R groups on one nitrogen atom are linked together to form a 3-8 membered monocyclic azacyclic ring or an 8-12 membered bicyclic fused azacyclic ring system, each of which may be saturated, unsaturated or aromatic and which may contain 1-3 heteroatoms independently selected from N, O and S as ring members, and which may be optionally substituted with the substituents described as suitable for alkyl groups or, if $NR_2$ comprises an aromatic group, it may be optionally substituted with the substituents described as typical for heteroaryl groups.

Amino groups may optionally be in a protected or unprotected form. One of skill in the art would appreciate that appropriate amine protecting groups may vary depending on the functionality present in the particular molecule and the nature of the amino group. Suitably protected amines may include, for example, amines protected as carbamates (e.g., tert-butoxycarbonyl (Boc), benzyloxycarbonyl (Cbz), fluorenylmethyloxy-carbonyl (Fmoc), allyloxycarbonyl (Alloc) or (trialkylsilyl)ethoxycarbonyl), carboxamides (e.g., formyl, acyl or trifluoroacetyl, benzoyl), sulfonamides, phthalimides, succinimides, Schiff's base derivatives, and the like. Also included are alkyl or allyl amines, as well as trialkylsilyl protected amines.

Where an amine is present in protected form, it is sometimes desirable to remove the protecting group. Thus, the methods of the present invention also optionally include a step of removing any protecting groups on an amine or aminoalkyl group.

The terms "alkylsulfonyl" and "arylsulfonyl" as used herein refer to moieties of the form —$SO_2$alkyl or —$SO_2$aryl, where alkyl and aryl are defined as above. For alkylsulfonyl groups, the alkyl moiety may contain 1-10 C (alkyl), preferably 1-8 C (alkyl), more preferably 1-4 C (alkyl). For arylsulfonyl groups, preferably the monocyclic aryl and heteroaryl groups contain 5-6 ring members, and the bicyclic aryl and heteroaryl groups contain 8-10 ring members. Optionally fluorinated $C_{1-4}$alkyl, and optionally substituted phenyl groups are particularly preferred for sulfonyl moieties. The phenyl groups of an arylsulfonyl moiety may be optionally substituted with one or more substituents suitable for an aryl ring; for example, they may be substituted by halo, methyl, nitro, alkoxy, amino, or the like. Such sulfonyl moieties, when present on oxygen form sulfonates. Such sulfonyl moieties form sulfonamides when present on nitrogen, and sulfones when present on carbon. Representative sulfonates include, e.g., —$OSO_2$Me (mesylate), —$OSO_2CF_3$ (triflate), —$OSO_2$tolyl (tosylate), and the like.

The term "alkoxycarbonyl" as used herein refers to a moiety of the form —COOR', where R' is C1-C8 alkyl, C2-C8 alkenyl, C5-C6 aryl, or C6-C14 arylalkyl, trialkylsilyl, or the like, each of which may be optionally substituted. When present on nitrogen, such alkoxycarbonyl moieties form carbamates, which are frequently used as nitrogen protecting groups. In some such embodiments, R' may be optionally halogenated C1-C4 alkyl (e.g., tert-butyl, methyl, ethyl, 2,2, 2-trichloroethyl, 1,1-dimethyl-2,2,2-trichloroethyl), allyl, optionally substituted benzyl, fluorenylmethyl, or trialkylsilyl (e.g., triisopropylsilyl, triethylsilyl, trimethylsilyl, tert-butyldimethylsilyl). When present on carbon, such moieties may also be referred to as carboxylate esters, carboalkoxy groups, or the like.

"Trialkylsilyl" as used herein refers to any of the well-known trialkylsilyl derivatives commonly used as protecting groups, such as for example, trimethylsilyl, triisopropylsilyl, triethylsilyl, tert-butyldimethylsilyl, and the like. Also intended to be encompassed within the scope of the invention are derivatives where one or more of the alkyl groups on silyl is replaced by phenyl, for example, tert-butyldiphenylsilyl, and other such groups known to one of skill in the art.

The term "substituted" means that the specified group or moiety bears one or more non-hydrogen substituents. The term "unsubstituted" means that the specified group bears no such substituents.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Alkyl, alkenyl and alkynyl groups are often substituted to the extent that such substitution makes sense chemically. Typical substituents include, but are not limited to, halo, OH, =O, =N—CN, =N—OR, =NR, OR, $NR_2$, SR, SOR, $SO_2$R, $SO_2NR_2$, $NRSO_2$R, $NRCONR_2$, NRCOOR, NRCOR, CN, COOR, $CONR_2$, OOCR, COR, and $NO_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR, =NR', OR, $NR'_2$, SR', SOR', $SO_2$R', $SO_2NR'_2$, NR'$SO_2$R', NR'CONR'$_2$, NR'COOR', NR'COR', CN, COOR', CONR'$_2$, OOCR', COR', and $NO_2$, wherein each R' is independently H, optionally fluorinated C1-C8 alkyl, C2-C8 heteroalkyl, C1-C8 acyl, C2-C8 heteroacyl, C5-C12 aryl, C5-C12 heteroaryl, C5-C20 arylalkyl, or C5-C20 heteroarylalkyl. Alkyl, alkenyl and alkynyl groups can also be substituted by C1-C8 acyl, C2-C8 heteroacyl, C5-C12 aryl or C5-C12 heteroaryl, each of which can be substituted by the substituents that are appropriate for the particular group. Preferred substituents when present on an alkyl, alkenyl or alkynyl group, or a heteroform of one of these, include halo, OH, =O, OR, SR, and $NR_2$, where R is defined as above.

Aryl and heteroaryl moieties may be substituted with a variety of substituents including optionally fluorinated C1-C8 alkyl, C2-C8 alkenyl, C2-C8 alkynyl, C5-C12 aryl, C1-C8 acyl, C5-20 arylalkyl, and heteroforms of these, each of which can itself be further substituted; other substituents for aryl and heteroaryl moieties include halo, OH, OR, $NR_2$, SR, SOR, $SO_2R$, $SO_2NR_2$, $NRSO_2R$, $NRCONR_2$, NRCOOR, NRCOR, CN, COOR, $CONR_2$, OOCR, C(O)R, and $NO_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl, or C5-C20 heteroarylalkyl, and each R is optionally substituted as described above for alkyl groups. The substituent groups on an aryl or heteroaryl group may of course be further substituted with the groups described herein as suitable for each type of group that comprises the substituent. Preferred substituents when present on an aryl or heteroaryl group include halo, OH, OR, SR, $NR_2$, CN, COOR, $CONR_2$, and $NO_2$, where R is defined as above.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

The present invention provides novel macrocyclic lactams of formula (I), which are key intermediates in the synthesis of diazonamide analogs. The invention also provides an efficient process for the preparation of these macrocyclic lactams, by electrochemical oxidation of a phenolic compound of formula (II). The invention also provides methods for further conversion of compounds of formula (I) into diazonamide analogs, in good chemical yields and with high diastereomeric purity.

Where chiral carbons are included in chemical structures, unless a particular orientation is depicted, both stereoisomeric forms are intended to be encompassed. Compounds of formulae (I) and (II) may, for example, have two or more asymmetric centers and therefore exist in different enantiomeric and/or diastereomeric forms. All optical isomers and stereoisomers of the compounds of formulae (I) and (II), and mixtures thereof, are considered to be within the scope of the invention. With respect to the compounds of formulae (I) and (II), the invention includes the use of a racemate, one or more enantiomeric forms, one or more diastereomeric forms, or mixtures thereof. The compounds of the invention may also exist as tautomers. This invention relates to the use of all such tautomers and mixtures thereof.

In certain embodiments of formula (I) and (II), the carbon atom bearing the substituent $R^1$ has the (S)-configuration. In other embodiments, where $R^3$ is a protected or unprotected amino group, the carbon atom bearing the substituent $R^3$ has the (S)-configuration.

In compounds of formula (I), $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted.

In compounds of formula (I), $R^1$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted.

In certain embodiments of formula (I), $R^1$ and $R^2$ may be taken together with the atoms to which they are attached to form a 5- or 6-member ring containing one nitrogen atom.

In compounds of formula (I), $R^3$ is H, or —$NR^4R^5$, where $R^4$ is H, or C1-C4 alkyl. In some embodiments, $R^5$ is H, or C1-C8 alkyl, C1-C8 heteroalkyl, C6-C14 arylalkyl, C6-C14 heteroarylalkyl, arylsulfonyl, trialkylsilyl, or alkoxycarbonyl, each of which may be optionally substituted. In other embodiments, $R^5$ is —C(=X)R' where X is O, S, or NH, and R' is optionally fluorinated C1-C8 alkyl, C2-C8 alkenyl, C5-C12 aryl, or C6-C14 arylalkyl, each of which may be optionally substituted.

In further embodiments, $R^4$ and $R^5$ may be taken together with nitrogen to form an imine, or an optionally substituted 3-8 membered monocyclic azacyclic ring or 8-12 membered bicyclic fused azacyclic ring, each of which may contain 0-2 additional heteroatoms selected from N, O, and S as ring members.

In compounds of formula (I), $R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted.

In compounds of formula (I), $R^7$ is H, or halo, —CN, optionally substituted C1-C6 acyl, —$COOR^8$, or —C(O)$NR^9_2$; wherein $R^8$ is H, or C1-C8 alkyl, C2-C8 alkenyl, C5-C6 aryl, C6-C14 arylalkyl, or trialkylsilyl; and each $R^9$ is independently H, or C1-C8 alkyl, C2-C8 alkenyl, C5-C6 aryl, C6-C14 arylalkyl, C6-C14 heteroarylalkyl, —OH, or C1-C4 alkoxy, each of which may be optionally substituted. In certain embodiments, two $R^9$ groups on the same N can optionally cyclize to form a ring; in specific embodiments, the ring is a 3-8 membered azacyclic ring optionally containing an additional heteroatom selected from N, O, and S as a ring member.

In compounds of formula (I), each of Y and Y' is independently H, or halo, —OH, or —$OR^{10}$, where $R^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted.

In frequent embodiments of formula (I), $R^3$ is a protected amino group of the form —$NR^4R^5$, where $R^5$ represents a protecting group. In certain preferred embodiments, $R^3$ is —$NR^4R^5$, where $R^4$ is H, and $R^5$ represents a carbamate protecting group (i.e., $R^3$ is a protected amino group of the form —NHCOOR'). In specific embodiments, the carbamate protecting group is tert-butoxycarbonyl (Boc), benzyloxycarbonyl (Cbz), allyloxycarbonyl (alloc), trimethylsilyl-ethoxycarbonyl (Teoc), 2,2,2-trichloroethoxycarbonyl (Troc), fluorenylmethylcarbonyl (Fmoc), or the like. In a particularly preferred embodiment, $R^3$ is —$NR^4R^5$, where $R^4$ is H, and $R^5$ is Cbz (i.e., $R^3$ is —NHCbz).

In other embodiments of formula (I), $R^3$ is an acylamino group of the form —NHC(=O)R', where R' is an optionally fluorinated C1-C8 alkyl, C2-C8 alkenyl, C5-C12 aryl, or C6-C14 arylalkyl group, each of which may be optionally substituted. In some such embodiments, R' is C1-C8 alkyl substituted with —OH, —OR", or —NHR", where R" is C1-C4 alkyl, C2-C4 alkenyl, C2-C6 acyl, C2-C6 aroyl, C5-C6 aryl, C5-C6 heteroaryl, or C6-C10 arylalkyl. In a preferred embodiment, $R^3$ is —NHC(=O)C(OH)iPr.

Frequently, when $R^3$ is a protected or unprotected amino group, the carbon atom bearing $R^3$ has the (S)-configuration.

In certain embodiments, $R^1$ is C1-C8 alkyl, and $R^2$ is H or C1-C4 alkyl. In a preferred embodiment, $R^1$ is C1-C4 alkyl, and $R^2$ is H or Me. In a particularly preferred embodiment, $R^1$ is isopropyl, and $R^2$ is H. In preferred embodiments, the carbon atom bearing substituent $R^1$ has the (S)-configuration.

In many embodiments, Y' is H or halo, and Y is halo or —OR$^{10}$, where $R^{10}$ is H, or is optionally fluorinated alkylsulfonyl or arylsulfonyl. In preferred embodiments, Y' is H, and Y is bromo or triflate (—OTf).

$R^6$ is preferably H, or an arylalkyl, arylsulfonyl, acyl or alkoxycarbonyl moiety.

In many embodiments, $R^7$ is —COOR$^8$, where $R^8$ is H, or C1-C4 alkyl. In a preferred embodiment, $R^7$ is —COOMe.

The groups described herein for $R^1$-$R^{10}$, Y and Y' in compounds of formula (I) are also suitable for compounds of formulae (IA), (IB), (IC), (II), (IIA), (IIB), (IIC), as further described herein.

In particular embodiments, the compound of formula (I) represents a compound having the formula (IA) or (IB):

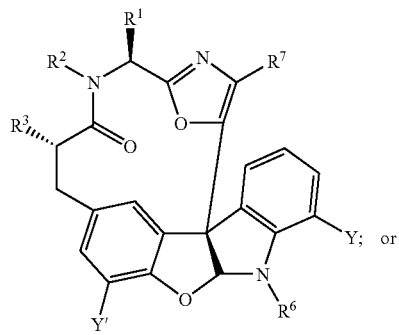

(IA)

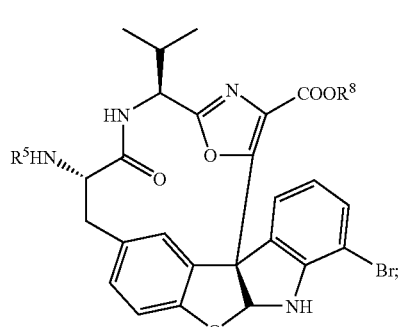

(IB)

wherein $R^1$, $R^2$, $R^3$, $R^5$, $R^6$, $R^7$, $R^8$, Y and Y' are defined as for formula (I).

In certain methods of the invention, compounds of formula (IA) and (IB) are prepared by electrochemical oxidation of a compound of formulae (IIA) or (IIB), respectively:

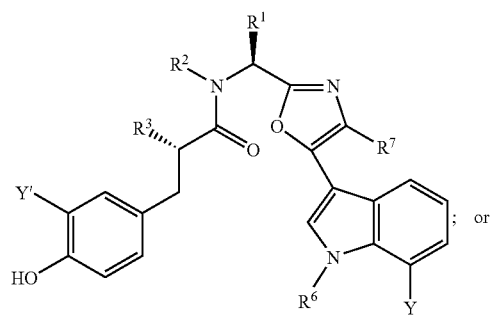

(IIA)

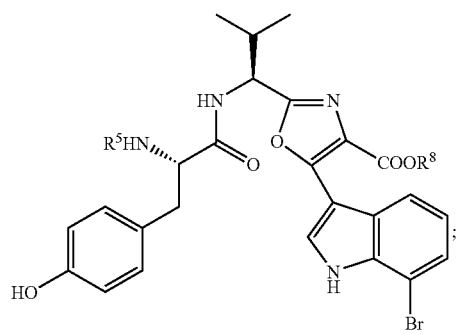

(IIB)

wherein $R^1$, $R^2$, $R^3$, $R^5$, $R^6$, $R^7$, $R^8$, Y and Y' are defined as for formula (I).

In one embodiment, the compound of formula (IA):

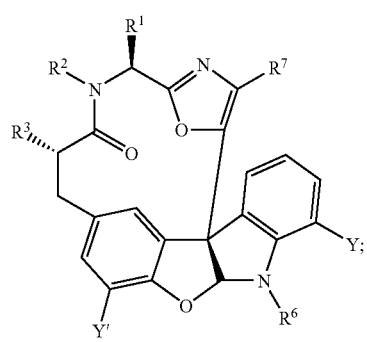

(IA)

wherein $R^3$ is —NR$^4$R$^5$; and
$R^1$, $R^2$, $R^4$, $R^5$, $R^6$, $R^7$, Y and Y' are defined as for formula (I);

is prepared by electrochemical oxidation of the compound of formula (IIA):

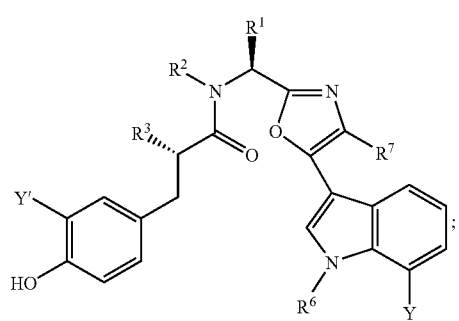

wherein $R^1$, $R^2$, $R^3$, $R^4$, $R^5$, $R^6$, $R^7$, Y and Y' are defined as for formula (IA).

In another embodiment, the compound of formula (IB):

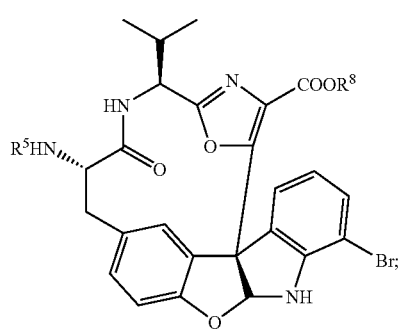

wherein $R^5$ is alkoxycarbonyl; and $R^8$ is H, or C1-C8 alkyl, C2-C8 alkenyl, C5-C6 aryl, C6-C14 arylalkyl, or trialkylsilyl;

is prepared by electrochemical oxidation of the compound of formula (IIB):

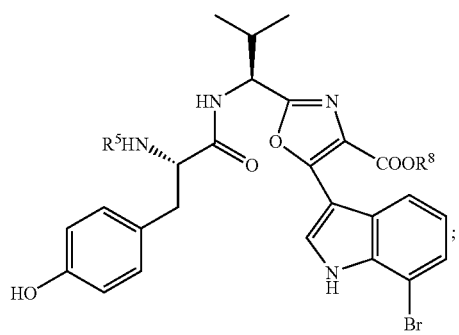

wherein $R^5$ and $R^8$ are defined as for formula (IB).

In another embodiment, the compound of formula (I) represents a compound having the formula (IC):

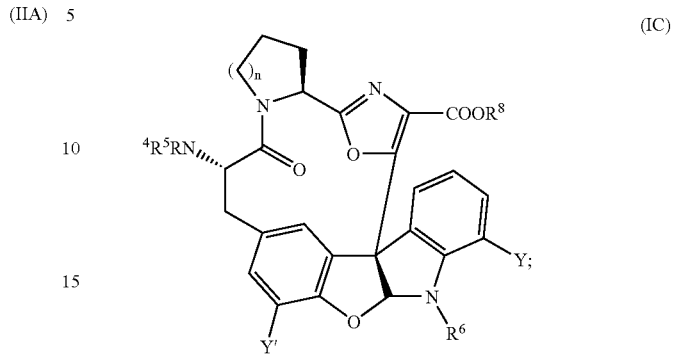

wherein $R^4$, $R^5$, $R^6$, $R^8$, Y and Y' are defined as for formula (I); and n is 1 or 2.

In certain methods of the invention, the compound of formula (IC):

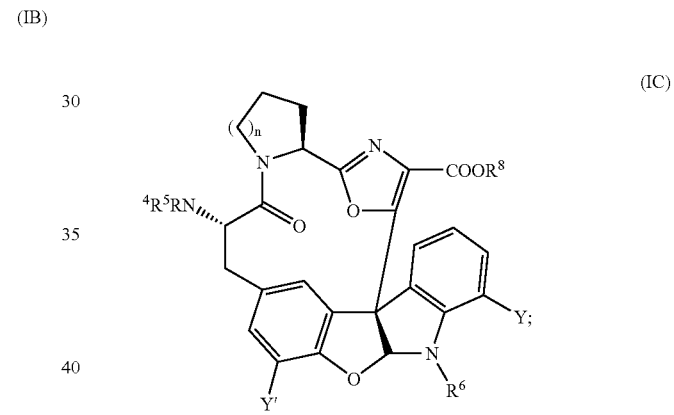

wherein $R^4$, $R^5$, $R^6$, $R^8$, Y and Y' are defined as for formula (I); and n is 1 or 2;

is prepared by electrochemical oxidation of the compound of formula (IIC):

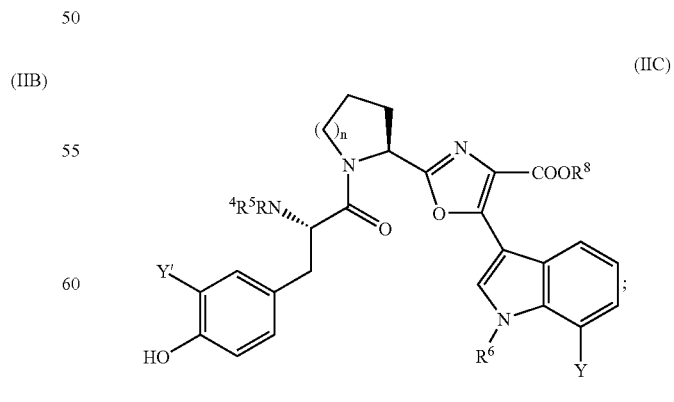

wherein n, $R^4$, $R^5$, $R^6$, $R^8$, Y and Y' are defined as for formula (IC).

In a preferred embodiment, the compound of formula (8b):

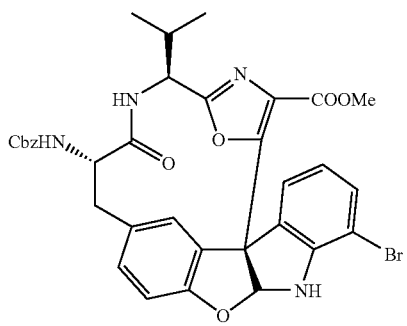

is prepared by electrochemical oxidation of the compound of formula (7b):

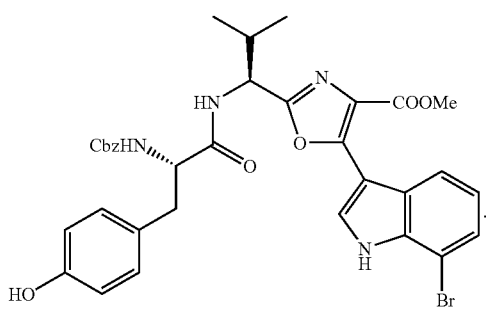

In certain embodiments, the method for preparation of a compound of formula (I), (IA), (IB), (IC) or (8b) by electrochemical oxidation of a compound formula (II), (IIA), (IIB), (IIC) or (7b), respectively, comprises an optional purification step, wherein the compound of formula (I), (IA), (IB), (IC) or (8b) is purified by chromatography, by recrystallization, by trituration, or by a combination of methods. In specific embodiments, the compounds of formula (I), (IA), (IB), (IC) or (8b) is purified by trituration with methyl-tert-butyl ether (MTBE) to give a single diastereomeric product with greater than 90% d.e.

In other embodiments, the method for preparation of a compound of formula (I), (IA), (IB), (IC) comprises an additional step for removing any protecting groups that are present at $R^2$, $R^3$, $R^6$ or $R^7$. In a particular embodiment, the method for preparation of a compound of formula (8b) comprises an additional step or steps for removing the Cbz protecting group and/or hydrolysis of the methyl ester.

In a particularly preferred embodiment, the compound of formula (8b) is purified by trituration of the product mixture with MTBE, filtration, and concentration of the filtrate in vacuo to provide the compound of formula (8b) in greater than 90% d.e.

The compounds of formula (I), (IA), (IB), (IC) and (8b) may be subsequently elucidated to provide diazonamide analogs with high diastereomeric purity and in good chemical yield.

In certain embodiments of the methods of the invention, electrochemical oxidization is carried out in an electrolyte that contains a conducting salt. In frequent embodiments, said conducting salt is a tetra($C_{1-6}$alkyl)ammonium salt, wherein the salt comprises at least one counterion which is a sulfate, hydrogensulfate, alkylsulfate, arylsulfate, aryl sulfonate, alkyl sulfonate, halide, phosphate, carbonate, alkylphosphate, alkylcarbonate, nitrate, alcoholate, tetrafluoroborate or perchlorate counterion. In a preferred embodiment, the conducting salt is tetraethylammonium tetrafluoroborate.

The methods of the invention can be carried out in any standard electrolysis cell that is known in the art. In preferred embodiments, the electrochemical oxidation is carried out in an undivided electrolysis cell.

Electrochemical oxidation methods of the invention are typically carried out at current densities of from about 5 to about 40 $mA/cm^2$, and at a voltage of from about 1 to about 5 volt. In preferred embodiments, the electrochemical oxidation was carried out at a potential of from about 1 to about 2 volts, more preferably from about 1.5 to about 1.7 volts.

Electrochemical oxidation is typically carried out from about 0° C. to about 60° C., preferably from about 10° C. to about 25° C. Frequently, it is conducted at ambient temperature.

In certain embodiments, the electrochemical oxidation is carried out in a solvent or mixture of co-solvents. Typical solvents are inert solvents having a high oxidation potential generally customary in organic chemistry.

Solvents for the electrochemical oxidation methods are frequently selected from the group consisting of dimethylformamide (DMF), dimethylacetamide (DMA), N-methyl pyrrolidinone (NMP), dimethylsulfoxide (DMSO), sulfolane, pyridine, nitrobenzene, acetonitrile, benzonitrile, a straight or branched chain C1-C4 alcohol, water, ethylene carbonate, propylene carbonate, 1,2-butylene carbonate, 2,3-butylene carbonate, vinylene carbonate, methyl formate, γ-butyrolactone, N,N-dimethylpropyleneurea (DMPU), 1,1,3,3-tetramethylurea, or 3-methyl-2-oxazolidinone, and mixtures thereof. In certain embodiments, the oxidation is carried out in a solvent medium consisting primarily of DMF; in a preferred embodiment, the solvent comprises at least 50% DMF.

Certain functional groups contained within the compounds of the present invention can be replaced by bioisosteric groups, that is, groups that have similar spatial or electronic requirements to the parent group, but exhibit differing or improved physicochemical or other properties. Suitable examples are well known to those of skill in the art, and include, but are not limited to moieties described in Patini et al., Chem. Rev., (1996), 96, 3147-3176 and references cited therein.

Preparation of Macrocyclic Lactams of Formula (I)

Figure 2:
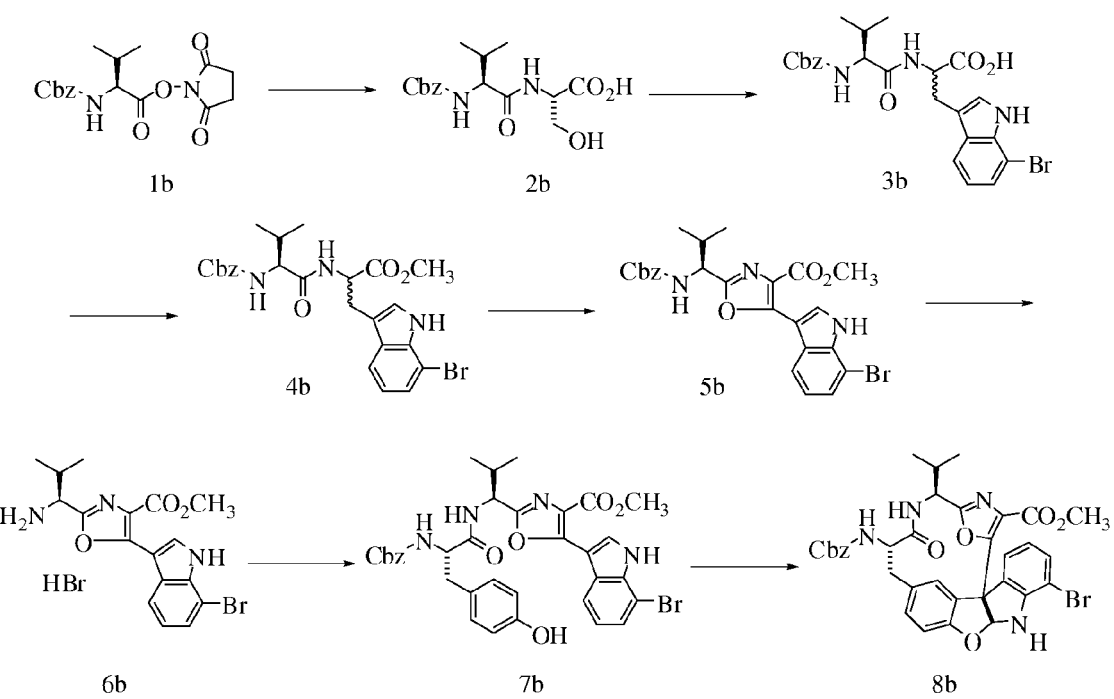
FIG. 2 shows a synthetic route for the preparation of the compound of formula (8b).

Macrocyclic lactams of formula (1) are prepared through a novel and efficient multi-step process, using methods such as those shown in FIG. 1 and FIG. 2. A key step in the process involves the electrochemical oxidative cyclization of a phenolic intermediate of formula (II) to provide the macrocyclic lactam of formula (1).

A prior route for preparation of compounds of formula (I) utilized phenyliodo(III) diacetate (PIDA) to carry out the oxidative cyclization of phenolic intermediates. However, this approach was complicated by low chemical yields, and complex purification, requiring multiple chromatographies, to remove the undesired diastereomer.

The methods of the present invention provide compounds of formula (I) in high yield and purity, without using an oxidative reagent such as PIDA. The present methods allow the efficient conversion, and therefore the use of lesser amounts of starting materials, as well as simplified separation and purification procedures, for preparation of compounds formula (I), which are key intermediates in the preparation of diazonamide analogs. In particular, the methods of the present invention provide access to the macrocyclic intermediates in good yield and with high diastereomeric purity, preferably in greater than 95% diastereomeric excess.

FIG. 1 provides a general synthetic route useful for the preparation of macrocyclic lactams of formula (1). The preparation of a specific compound of formula (8b) is presented in FIG. 2, and in the Examples.

As shown in FIGS. 1 and 2, dipeptide starting materials of formula (2a) or (2b) are prepared under standard conditions known in the art, for example, by coupling an N-hydroxysuccinimide ester or another activated ester of a protected amino acid with serine. It will be understood by one of skill in the art that a wide variety of suitable conditions may be utilized to form the dipeptide starting materials, including the extensive body of literature describing synthesis of peptides and peptide mimetics.

A novel indolation reaction is utilized to install an optionally functionalized indole moiety. A dipeptide of formula (2a) or (2b) is reacted with an optionally substituted indole and an activating reagent, optionally in the presence of a protic acid, to provide a compound of formula (3a) or (3b). The reaction can be carried out at a temperature ranging from about 0° C. to about 150° C., preferably from about 25° C. to about 100° C., more preferably from about 40° C. to about 80° C.

Without wishing to be bound by theory, it is believed that the reaction proceeds by dehydration to form an acrylic acid derivative, followed by Michael addition and rearomatization of the indole nucleus.

Suitable activating reagents include, for example, carboxylic acid anhydrides, mixed anhydrides, or acyl halides (e.g., acetic anhydride, trifluoroacetic anhydride, acetyl chloride, oxalyl chloride), sulfonic acid anhydrides or halides (e.g., methanesulfonic anhydride, trifluoromethanesulfonic anhydride, methanesulfonyl chloride), mineral acid halides (e.g., thionyl chloride, or phosphoryl chloride), and the like.

In a preferred embodiment, the activating agent is acetic anhydride, and the reaction is conducted in acetic acid as a protic solvent. In a particularly preferred embodiment, the dipeptide of formula (2a) or (2b) and an optionally substituted indole are reacted with acetic anhydride in acetic acid at about 80° C., to provide the compound of formula (3a) or (3b).

The preparation of N-acetyl tryptophan derivatives by reaction of serine or N-acetyl serine and an optionally substituted indole in acetic anhydride and acetic acid has been previously reported. Y. Yokoyama, et al., *Tetrahedron Letters* (1999), 40: 7803; Y. Yokoyama, et al., *Eur. J. Org. Chem.* (2004), 1244; Y. Konda-Yamada, et al., *Tetrahedron* (2002), 58: 7851; M. W. Orme, et al., U.S. Pat. No. 6,872,721. However, the preparation of other acylated tryptophan derivatives under these conditions, such as the dipeptide analogs of the present invention, has not been previously described.

Esterification of the free carboxylic acid, followed by oxidative cyclization of the dipeptide intermediate with an oxidizing agent, for example, DDQ, provides an oxazole intermediate of formula (5a) or (5b). It will be understood by those in the art that other oxidative conditions could be utilized, such as, for example, 7,7,8,8-tetracyanoquinodimethane (TCNQ), ceric ammonium nitrate, hypervalent iodide reagents, and the like.

Deprotection of the protected amino group, if present, and amide bond formation provides a phenolic intermediate of formula (7a) or (7b). Electrochemical oxidative cyclization of phenolic compounds of formula (7a) or (7b) provides the macrocyclic lactam of formula (8a) or (8b). Such macrocyclic lactams are key intermediates in the synthesis of diazonamide analogs.

Electrolysis can be carried out in a divided or undivided electrochemical cell. The undivided cell is preferred unless the reactants or product are susceptible to reduction at the cathode.

In one embodiment, an electrochemical cell was assembled using a 1500-mL beaker and a custom polypropylene rack which supported 24 vertical graphite rods (6.15 mm diameter×150 mm length), arranged in an approximately circular pattern, with 7 mm between the sides of the rods; electrical connections were made such that the electrodes were in an alternating pattern of two anodes and one cathode.

In another embodiment, an electrochemical cell was assembled using a polyethylene cylinder (15 cm diameter and 30 cm height) and a custom rack (polypropylene and nylon) which supported 48 vertical graphite rods (6.15 mm diameter×30 cm length), arranged in a pattern of three concentric rings with 12 and 24 anodes in the inner and outer rings, respectively. The intermediate ring contained 12 cathodes, separated from adjacent anodes by approximately 7 mm. The electrodes were immersed to a depth of 24 cm.

In preferred embodiments, the solution was stirred vigorously during the electrochemical oxidation step.

Suitable cathode materials are, for example, iron, steel, stainless steel, nickel or noble metals such as platinum, and graphite or carbon materials.

Suitable anode materials are, for example, noble metals such as platinum, or metal oxides such as ruthenium or chromium oxide or mixed ruthenium-titanium oxides, and the like. The anode may also be selected from known materials such as glassy carbon, graphite, etc.

Systems using graphite or carbon as anode and cathode, or graphite or carbon as an anode and nickel, stainless steel or steel as a cathode are generally preferred. In a preferred embodiment, both the anode and cathode are graphite.

To carry out the electrochemical oxidation reaction of the invention, direct or substantially direct current is applied to the electrodes. Current is applied for a time sufficient to pass the theoretical amount of coulombs required to oxidize at least a portion of the phenolic starting material. Theoretically, at 100% current efficiency, two moles of electrons (i.e. 2×96,500 coulombs=193,000 coulombs) are consumed in oxidizing one mole of phenolic starting material; at 140% theoretical current, 2.8 moles of electrons would be required. Preferably, to facilitate complete reaction, current is generally applied for a time sufficient to pass about 130-140% of theoretical current.

The current densities at which the process is carried out are in general from 1 to 1000 mA/cm$^2$, preferably from 5 to 100 mA/cm$^2$, and more preferably from about 5 to about 40 mA/cm$^2$.

The voltage is generally from about 0.5 to about 10 volts, preferably from 1 to 5 volts. In preferred embodiments, the electrochemical oxidation was carried out at a potential of from about 1 to about 2 volts, more preferably from about 1.5 to about 1.7 volts.

The phenolic starting material of formula (II) is dissolved in a suitable solvent, such as, for example, DMF, DMA, NMP, DMSO, DMPU, sulfolane, pyridine, an alcohol, water, ethylene carbonate, or another appropriate solvent. In a preferred embodiment, the solvent is at least about 50% DMF.

If desired, a suitable conducting salt may also be included in the electrolysis solution. Examples of suitable conducting salts include, alkali metal or tetra($C_{1-6}$alkyl)-ammonium salts, preferably tri($C_{1-6}$alkyl)methylammonium or tetraethylammonium salts. Suitable counterions include sulfate, hydrogensulfate, alkylsulfate, arylsulfate, halide, phosphate, carbonate, alkylphosphate, alkylcarbonate, nitrate, alcoholate, tetrafluoroborate or perchlorate. The acids derived from the abovementioned anions are also suitable as conducting salts. In a preferred embodiment, the conducting salt is tetraethylammonium tetrafluoroborate.

A base, for example an alkali metal salt of an alcohol or water, e.g., aqueous potassium hydroxide, sodium methoxide in methanol, or potassium ethoxide in ethanol, is added to the solution in the electrolysis cell. In certain embodiments, the base is 0.1-10 N aqueous potassium or sodium hydroxide; in a preferred embodiment, it is 0.5-5 N aqueous potassium hydroxide.

If appropriate, customary solvents and co-solvents may be added to the electrolysis solution. These are inert solvents having a high oxidation potential generally customary in organic chemistry. Examples of suitable solvents include dimethylformamide (DMF), dimethylacetamide (DMA), N-methylpyrrolidinone (NMP), dimethylsulfoxide (DMSO), sulfolane, pyridine, nitrobenzene, acetonitrile, benzonitrile, a straight or branched chain C1-C4 alcohol, water, ethylene carbonate, propylene carbonate, 1,2-butylene carbonate, 2,3-butylene carbonate, vinylene carbonate, methyl formate, γ-butyrolactone, N,N-dimethylpropyleneurea (DMPU), 1,1,3,3-tetramethylurea, 3-methyl-2-oxazolidinone, and mixtures thereof.

In frequent embodiments, the electrochemical oxidation is conducted in a solvent medium consisting primarily of a solvent selected from the group of solvents described above. In a preferred embodiment, the electrochemical oxidation is carried out in a solvent medium comprising at least 50% DMF.

The temperatures for the electrochemical oxidation are customarily from −20° C. to 100° C., preferably from 0° C. to 60° C., more preferably from about 10° C. to about 25° C. Frequently, the electrochemical oxidation is conducted at ambient temperature. In general, the process is carried out at ambient pressure of about 1 bar. Higher pressures are preferably used if the process is to be carried out at higher temperatures in order to avoid boiling of the starting compounds and/or co-solvents.

The electrochemical oxidation may be carried out on a single charge of the phenolic starting material, by charging the electrochemical cell once with the starting material and base, followed by electrochemical oxidation until the oxidation reaction is substantially complete. In an alternative embodiment, multiple charges of phenolic starting material and base may be added to the electrochemical cell over the course of several days, followed by electrochemical oxidation of the reaction mixture after the addition of each charge of starting material.

The disappearance of starting material is monitored, typically by HPLC, TLC, or other standard approaches known in the art, and the electrolysis operation is ended once the reaction has reached substantial completion. After completion of the reaction, the electrolysis solution is worked up according to general separation methods, as further described herein. The desired products of formula (I) are typically produced as a ca. 80:20 to 90:10 mixture of diastereomers, resulting from selective diastereofacial addition of the phenolic ring to the indole nucleus. In certain embodiments, the diastereomeric ratio is determined by HPLC integration at 220 nM. Further purification can be carried out, for example, by crystallization, distillation or chromatography, or a combination of methods. Individual diastereomeric products can be isolated, for example, by recrystallization, trituration, or chromatographically, or a combination of methods. Preferably, the intermediates are purified to provide the isolated macrolactams in a greater than 90:10 ratio of desired to undesired diastereomeric products (80% diastereomeric excess; 80% d.e.); more preferably, the intermediates are purified to provide the isolated macrolactams in a greater than 95:5 ratio (90% d.e.); still more preferably in a greater that 99:1 ratio (98% d.e.).

In one embodiment, the product of formula (8b) was purified by flash column chromatography to provide the product as a mixture of diastereomers in a ratio of ~84:14, as measured by HPLC integration at 220 nm. The product was further purified by trituration with methyl t-butyl ether (MTBE), followed by filtration and washing with additional portions of MTBE. HPLC analysis of the filtrate showed a ~95:2 ratio of stereoisomers (as measured by integration at 220 nm). The filtrate was evaporated and dried under vacuum, to provide the isolated product of formula (8b) with enriched diastereomeric purity, having greater than 95% d.e.

Without wishing to be bound by theory, it is believed that the relative stereochemistry of the oxidative cyclization reaction is controlled by the stereocenter present at the carbon atoms bearing the substituent $R^1$ and/or $R^3$, which controls the diastereofacial addition of the phenolic ring to the indole nucleus. Absolute stereochemistry of the oxidative cyclization may be controlled by selection of the appropriate chiral starting material. In preferred embodiments, the carbon atoms bearing $R^1$ and $R^3$ possess the (S)-configuration.

Preparation of Diazonamide Analogs

Figure 3:
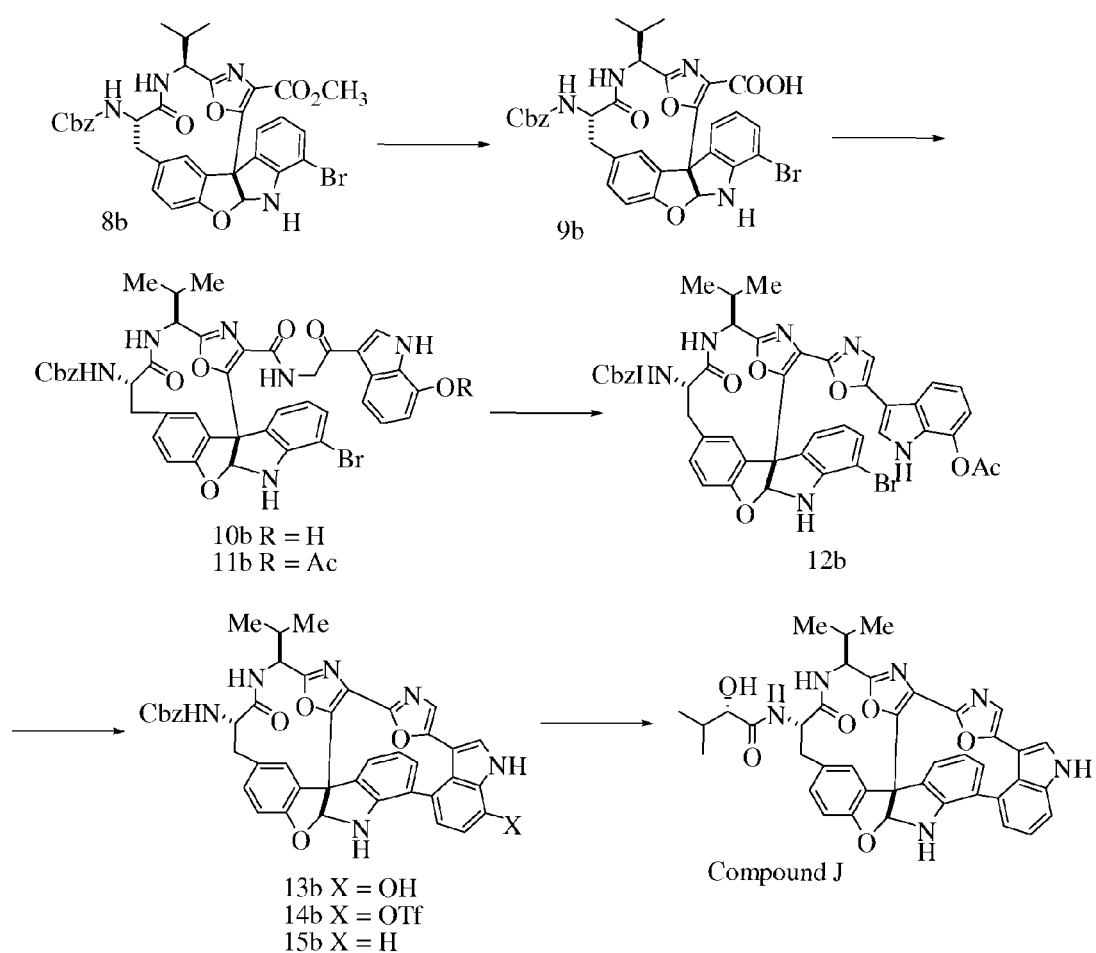
FIG. 3 shows a synthetic route for the preparation of Compound J.

Macrocyclic lactams of formula (1) can be further elucidated to provide diazonamide analogs. The preparation of a representative diazonamide analog, Compound J, is provided in FIG. 3 and in the Examples.

The diastereomerically enriched product of formula (8b), prepared as described above, was used in the subsequent conversion steps, providing access to diazonamide analogs in good chemical yields and with high diastereomeric purity.

The present invention will be further illustrated in the following, non-limiting examples.

In the examples described below, unless otherwise indicated all temperatures are set forth in degrees Celsius (° C.) and all parts and percentages are by weight. Reagents were purchased from commercial suppliers such as Aldrich Chemical Company or Lancaster Synthesis Ltd. and were used without further purification unless otherwise indicated.

Work-ups were typically done by doubling the reaction volume with the reaction solvent or extraction solvent and then washing with the indicated aqueous solutions using 25% over anhydrous $Na_2SO_4$ and/or $Mg_2SO_4$ prior to filtration and evaporation of the solvents under reduced pressure on a rotary evaporator.

$^1$H-NMR spectra were recorded on a Bruker or Varian instrument operating at 300, 400 or 500 MHz. $^1$H-NMR spectra were obtained as $CDCl_3$ solutions (reported in ppm), using chloroform as the reference standard (7.27 ppm), or in DMSO-d6 or $CD_3OD$ (3.4 and 4.8 ppm), or using tetramethylsilane (0.00 ppm) as an internal standard, when appropriate. Other NMR solvents were used as needed.

Mass spectrometry (MS) was conducted with various techniques. Mass spectra were typically obtained using liquid chromatograph electrospray ionization mass spectrometry, MS (ESP).

The following examples show how macrocyclic compounds of the invention were made according to the general synthetic pathways shown in FIGS. 1-2 according to the detailed experimental procedures that follow. Where appropriate, the reactions were also assayed by HPLC. These synthetic pathways and experimental procedures utilize many common chemical abbreviations, such as MTBE (methyl t-butyl ether), THF (tetrahydrofuran), DMF (N,N-dimethylformamide), EtOAc (ethyl acetate), EDC (1-(3-dimethylaminopropyl)-3-ethyl-1carbodiimide hydrochloride), DHOBT (3,4-dihydro-3-hydroxy-4-oxo-1,2,3-benzotriazine), HOBT (1-hydroxybenzotriazole hydrate), DIEA (diisopropylethylamine), DDQ (dichlorodicyanoquinone), Cbz (carbobenzyloxy), and the like.

Example 1

7-Bromoindole

2-Bromonitrobenzene (1.10 kg, 5.45 mol) was dissolved in tetrahydrofuran (10 L) at room temperature. This solution was cooled with stirring in a bath maintained at −78° C. When the internal temperature reached −40° C., vinylmagnesium bromide (16.3 L, 16.3 mol) was added at such a rate as to maintain the internal temperature at −40° C. during the addition. Upon complete addition, the reaction was removed from the bath and allowed to warm slowly to −30° C. over the course of 45 minutes. This required occasional cooling. The −30° C. reaction solution was quenched by rapid addition of a slightly cool (~10° C.) solution of saturated aqueous NH$_4$Cl (10 L). Slight foaming occurred. (Inverse quench into the ammonium chloride solution is also satisfactory.) This resulted in a biphasic mixture with some undissolved magnesium salts in the form of a gel. The mixture was stirred for 30 minutes and separated. The aqueous layer was back extracted with tetrahydrofuran (10 L). The combined organic layers were evaporated at reduced pressure with a bath temperature of 35° C. and the resulting dark oil was taken up in methylene chloride (5 L) and dried with Na$_2$SO$_4$. The mixture was filtered and concentrated. The resulting material was chromatographed, eluting with 2% ethyl acetate-hexanes to give 7-bromoindole (557 g, 52% yield) as an off-white solid. $^1$H NMR (CDCl$_3$): consistent with proposed structure.

Example 2

Cbz-Val-Ser-OH

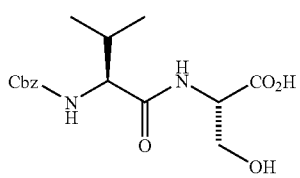

C$_{16}$H$_{22}$N$_2$O$_6$
FW: 338.36

L-Serine (104.19 g, 991 mmol) was dissolved in water (1440 mL) in a 4-L Erlenmeyer flask. Solid NaHCO$_3$ (83.25 g, 991 mmol was added and the mixture was stirred at room temperature to give a clear solution. Cbz-Val-OSu (300.0 g, 861 mmol) was added as a solution in 1,4-dioxane (1500 mL), with additional 1,4-dioxane (220 mL) used to rinse. The resulting cloudy mixture became clear after 1.5 h of stirring at 25° C. After 44 h, the mixture was divided into two equal portions. Methanol (700 mL) and 12 N aqueous HCl (42 mL, 504 mmol) was added to each portion, followed by EtOAc (1000 mL) and a solution of NaCl (100 g) dissolved in water (600 mL). The layers were separated and the organic layer was washed with saturated aqueous NaCl (350 mL). The aqueous layers were extracted in succession with EtOAc (1000 mL). The organic layers resulting from work-up of both portions of the reaction were combined, dried (Na$_2$SO$_4$), filtered, and evaporated to give a white solid (351 g). This material was suspended in CH$_2$Cl$_2$ (1500 mL) and stirred for 2 h. The mixture was filtered and the crystals were washed with CH$_2$Cl$_2$ (1000 mL) to give compound 2b as white crystals (262.3 g, 90% yield). $^1$H NMR (300 MHz, DMSO-d$_6$): consistent with proposed structure for compound 2b. MS: m/z=339.1 (M+1).

Example 3

Cbz-Val-(7-Bromo-Trp)-OH

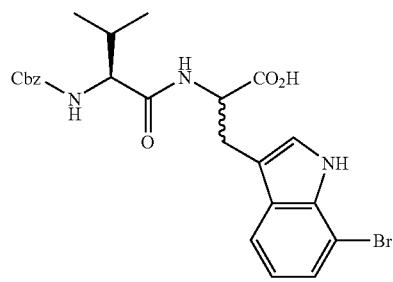

C$_{24}$H$_{26}$BrN$_3$O$_5$
FW: 516.38

Acetic acid (180 mL) was added to Cbz-Val-Ser-OH (42.89 g, 127 mmol) and 7-bromoindole (30.96 g, 158 mmol) in a round-bottom flask fitted with a mechanical stirrer, reflux condenser, and internal thermometer. Acetic anhydride (40 mL, 43 g, 420 mmol) was added and the mixture was heated to 80° C. over 40 min. Heating was continued at this temperature for 4 h. After cooling to room temperature and standing overnight, the mixture was diluted with ethyl ether (180 mL) and stirred for 30 min. The mixture was filtered and the crystals were washed with ethyl ether (250 mL). Drying of the crystals yielded product 3b (42.49 g, 65% yield). $^1$H NMR (300 MHz, DMSO-d$_6$): consistent with proposed structure for compound 3b. MS: m/z=516.0 (M+1).

Example 4

Cbz-Val-(7-Bromo-TrM)-OMe

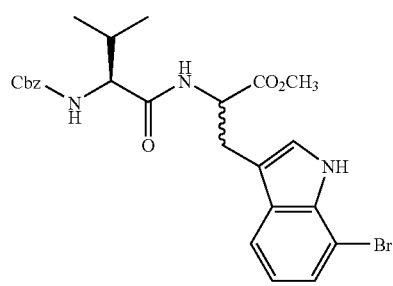

C$_{25}$H$_{28}$BrN$_3$O$_5$
FW: 530.41

Concentrated aqueous HCl (60 mL, 720 mmol) was added to a stirred suspension of starting material 3b (32.53 g, 63.0 mmol) in 2,2-dimethoxypropane (1200 mL, 1020 g, 9.8 mol).

After stirring for 24 h at 25° C., most of the solvent was evaporated to give wet crystals. MTBE (250 mL) was added and the mixture was allowed to stand with occasional swirling over 3 h. Filtration and washing of the crystals with MTBE (100 mL) gave product 4b (30.31 g, 91% yield). $^1$H NMR (300 MHz, DMSO-$d_6$): consistent with proposed structure for compound 4b. MS: m/z=530.1 (M+1).

Example 5

Methyl 2-((S)-1-(benzyloxycarbonylamino)-2-methylpropyl)-5-(7-bromo-1H-indol-3-yl)oxazole-4-carboxylate

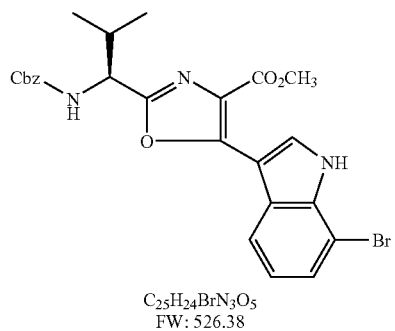

$C_{25}H_{24}BrN_3O_5$
FW: 526.38

A solution of DDQ (28.41 g, 125 mmol) in tetrahydrofuran (251 g, 282 mL) was added to starting material 4b (30.20 g, 56.9 mmol) in tetrahydrofuran (848 g, 954 mL) and the dark solution was heated to gentle reflux in an oil bath at 85° C. for 6 h. After cooling and standing overnight at room temperature, the solvent was removed on a rotary evaporator. Methanol (200 mL) was added and the solvent was evaporated to leave a brown crusty solid (91 g). Methanol (200 mL) was added and the solid was loosened with a spatula. The mixture was swirled until the appearance changed to a red liquid containing a yellow precipitate. The mixture was filtered and the precipitate was washed with methanol (60 mL). The pale gray crystals were air dried and then dried under vacuum to give product 5b (17.98 g, 60% yield). $^1$H NMR (300 MHz, DMSO-$d_6$): consistent with proposed structure for compound 5b. MS: m/z=526.0 (M+1).

Example 6

Methyl 2-((S)-1-amino-2-methylpropyl)-5-(7-bromo-1H-indol-3-yl)oxazole-4-carboxylate hydrobromide

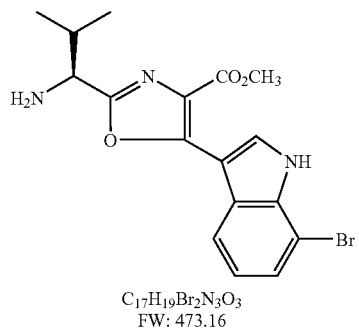

$C_{17}H_{19}Br_2N_3O_3$
FW: 473.16

Glacial acetic acid (25 mL) was added to starting material 5b (9.99 g, 19.0 mmol) in a 500-mL round-bottom flask fitted with a mechanical stirrer. The suspension was stirred at 25° C. and 33% HBr in acetic acid (50 mL) was added in one portion. The mixture became homogeneous and then a precipitate formed in 5-10 min. After 1 h, MTBE (235 mL) was added and stirring was continued at 25° C. for another 1 h 20 min. The mixture was filtered and the precipitate was washed with MTBE (150 mL). The cream-colored powder was dried under vacuum to give product 6b (8.91 g, 99% yield). $^1$H NMR (300 MHz, DMSO-$d_6$): consistent with proposed structure for compound 6b. MS: m/z=392.0 (M+1).

Example 7

Methyl 2-((S)-1-((S)-2-(benzyloxycarbonylamino)-3-(4-hydroxyphenyl)propanamido)-2-methylpropyl)-5-(7-bromo-1H-indol-3-yl)oxazole-4-carboxylate

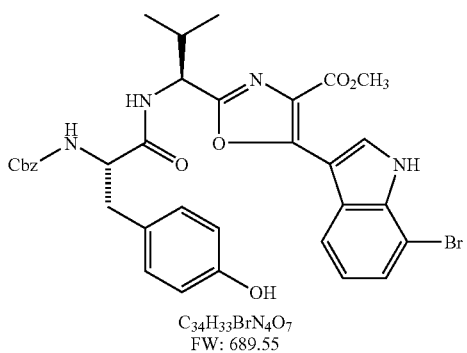

$C_{34}H_{33}BrN_4O_7$
FW: 689.55

DMF (100 mL) was added to the starting material 6b (9.16 g, 19.4 mmol), HOBt (3.17 g, 23.5 mmol), and Cbz-Tyr-OH (6.44 g, 20.4 mmol) in a round-bottom flask. Diisopropylethylamine (4.22 mL, 3.13 g, 129 mmol) was added, followed by EDC (4.15 g, 21.6 mmol). After stirring for 24 h at 25° C., the solution was diluted with EtOAc (500 mL) and the mixture was washed with 1 N aqueous HCl (250 mL), saturated aqueous sodium bicarbonate (250 mL), and saturated aqueous sodium chloride (250 mL). The solution was dried ($Na_2SO_4$), decanted, and evaporated to give a tan solid. This material was dissolved in 2-PrOH (180 mL) at 90° C. Hexanes (85 mL) were added and the solution was allowed to cool to room temperature. After standing overnight, the mixture was cooled to 5° C. for 4 h. The solid was separated by filtration and washed with 1:1 2-PrOH/hexanes (140 mL). This material, which at this point held residual solvent, was dried on a vacuum manifold to give product 7b (11.58 g, 87% yield). $^1$H NMR (300 MHz, DMSO-$d_6$): consistent with proposed structure for compound 7b. MS: m/z=689.0 (M+1).

Example 8

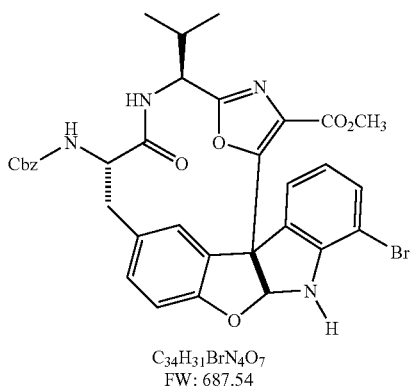

$C_{34}H_{31}BrN_4O_7$
FW: 687.54

An electrochemical cell was assembled using a 1500-mL beaker and a custom polypropylene rack which supported 24 vertical graphite rods (6.15 mm diameter×150 mm length). The rods were arranged in an approximately circular pattern with 7 mm between the sides of the rods. Electrical connections were made such that the electrodes were in an alternating pattern of two anodes and one cathode. The phenolic starting material 7b (5.00 g, 7.25 mmol) and $Et_4NBF_4$ (10.00 g, 46.1 mmol) were dissolved in DMF (1100 mL) in the beaker, and 0.5 N aq. KOH (15 mL, 7.5 mmol) was added, resulting in electrode immersion depth of 11 cm. The solution was stirred vigorously with a 4-bladed turbine (50 mm diameter, blades at 45° angle to shaft, approx. 500 rpm). The electrochemical reaction was carried out for 5.3 days at a constant potential of 1.7 volts. At that point approximately 1.26 amp-h of current had passed, and only 6.5% of the original starting material remained as determined by HPLC integration at 220 nM. The reaction mixture was concentrated on a rotary evaporator (bath temp. ≦35° C.) and dried further on a vacuum manifold. The residue was partitioned between EtOAc (250 mL) and 1 N aq. HCl (100 mL). The organic layer was washed with saturated aq. $NaHCO_3$ (50 mL) and then saturated aq. NaCl (50 mL). The aq. layers were extracted in succession with EtOAc (100 mL). The combined organic layers were dried ($Na_2SO_4$), decanted and evaporated to give 4.85 g of crude product. Flash column chromatography on silica gel (50 g), eluting with 25% EtOAc in $CH_2Cl_2$ gave 1.87 g (38% yield) of product 8b as a mixture of stereoisomers (81:19 as measured by HPLC integration at 220 nM).

Example 9

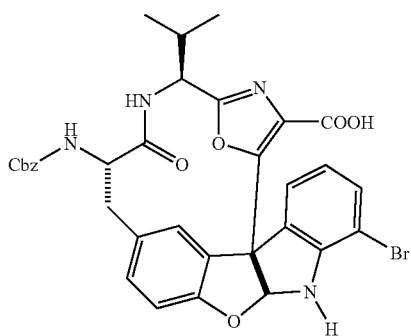

To a 1-L three-neck round-bottom flask equipped with a thermometer, an addition funnel and a magnetic stir bar was added the starting methyl ester (6.92 g, 10.03 mmol, containing ca. 80% of diastereomer 8b) and methanol (240 mL). The solution was cooled to 5° C. in ice-water bath followed by addition of lithium hydroxide in water (2.40 g/44 mL, 100.3 mmol, 10 eq.) at 5-10° C. with stirring. After addition the reaction mixture became a slurry. The cooling bath was removed and the mixture was allowed to warm to room temperature. The precipitate disappeared gradually. After 4.5 h stirring at room temperature less than 2% of starting material remained as determined by LCMS. Ice (440 g) was added to the reaction mixture and $HCl/H_2O$ (1 N, 105 mL) was added dropwise from an addition funnel with vigorous stirring to acidify the 0° C. reaction mixture. The pH of the mixture was adjusted to 2.5-3.0. A pale yellow solid precipitated, which was extracted using EtOAc (400 mL). The aqueous phase was concentrated to remove most of the methanol and then extracted with EtOAc (2×100 mL). The combined organic layers was dried over $Na_2SO_4$ and concentrated to afford crude product 9b (6.43 g, 9.6 mmol, as a ca. 80:20 mixture containing by-product hydantoin) which was used directly in the next step without further purification. $^1$H NMR (400 MHz, $CDCl_3$): consistent with proposed structure for compound 9b. MS: m/z=673.2 (M+1).

Example 10

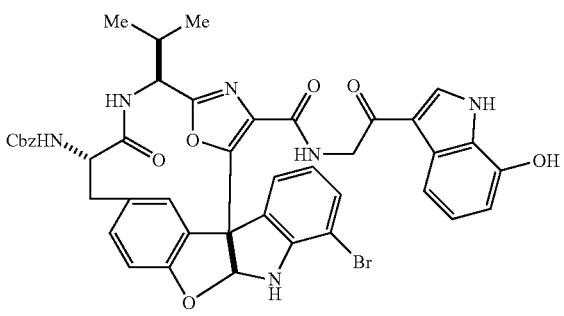

To a dry 250-mL round-bottom flask with magnetic stir bar was added DHOBt (545 mg, 3.34 mmol, 0.35 eq.), EDC HCl (2.75 g, 14.32 mmol, 1.5 eq.), anhydrous DMF (130 mL) and TEA (2.0 mL, 14.32 mmol, 1.5 eq.). The resulting reagent mixture was stirred for 20 min. To another dry 500-mL round-bottom flask was added the crude compound 9b (6.43 g, 9.6 mmol), 2-amino-1-(7-hydroxy-1H-indol-3-yl)ethanone hydrochloride (3.25 g, 14.32 mmol, 1.5 eq.) and DMF (30 mL). Then TEA (2.0 mL, 14.32 mmol, 1.5 eq) was added dropwise followed by the addition of the reagent mixture above. The resulting reaction mixture was stirred for 6 h at 40-42° C. and cooled to room temperature overnight. About 4% of starting acid remained as determined by LCMS. Most of DMF was removed under vacuum at 45° C. Less than 1% of starting material remained. The residue was diluted with EtOAc (800 mL)/water (200 mL). Some undissolved brown solid was removed by filtration. The organic phase was separated and the aqueous phase was extracted by EtOAc (2×100 mL). The combined organic layers were washed by water (100 mL), 10% aqueous $NaHSO_4$ (100 mL), water (100 mL), saturated $NaHCO_3$ (100 mL), water (2×100 mL) and brine (100 mL), and then dried over $Na_2SO_4$. After concentration the crude product 10b (8.4 g, 9.6 mmol) was obtained and used directly in next step without further purification. $^1$H NMR (400 MHz, $CDCl_3$): consistent with proposed structure for compound 10b. MS: m/z=845.1 (M+1).

Example 11

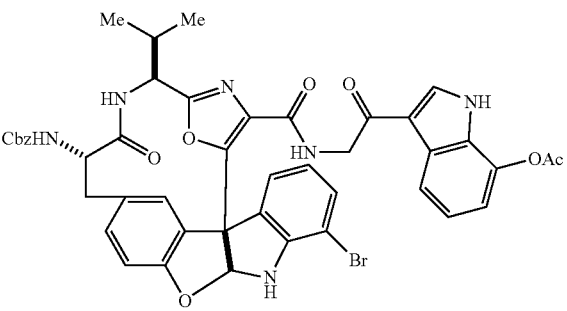

To a dry 500-mL flask containing crude compound 10b (8.4 g, 9.6 mmol) was added anhydrous tetrahydrofuran (40 mL) and anhydrous $CH_2Cl_2$ (150 mL). The resulting solution was cooled to 0° C. in ice-water bath. Acetic anhydride (2.69 mL, 28.65 mmol, 3.0 eq.) and pyridine (1.16 mL, 14.33 mmol, 1.5 eq.) were added sequentially at 0° C. Then the mixture was allowed to warm to room temperature and stirred under $N_2$. The reaction was monitored using LCMS. After 3.5 h only 2% of starting material was not consumed and 2% of over-acetylated product was formed. The reaction solution was diluted with ethyl acetate (700 mL) followed by washing with water (3×100 mL) and brine (100 mL) and drying over $Na_2SO_4$. After concentration, crude product 11b was purified by flash chromatography eluting with a EtOAc-$CH_2$ $Cl_2$ gradient (30/70 to 35/65) to afford desired product 11 (4.56 g, 5.14 mmol, 51% yield over three steps) from compound 8b which was 80% pure. $^1$H NMR (400 MHz, $CDCl_3$): consistent with proposed structure for compound 11b. MS: m/z=887.1 (M+1).

Example 12

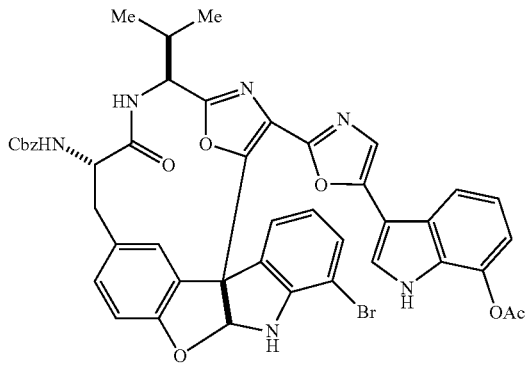

Triphenylphosphine (13.48 g, 51.4 mmol, 10 eq.) and hexachloroethane (12.17 g, 51.4 mmol, 10 eq.) were added to a dry 1-L three-neck round-bottom flask equipped with a thermometer, an addition funnel and a magnetic stir bar. Anhydrous $CH_2$ $Cl_2$ (320 mL) was added and the resulting solution was cooled to 10° C. in ice-water bath under $N_2$. TEA (10.03 mL, 71.96 mmol, 14 eq.) was added slowly to the solution, followed by stirring for 10 min at 10° C. The solution of compound 11b (4.56 g, 5.14 mmol, 1 eq.) in anhydrous $CH_2$ $Cl_2$ (160 mL) was added dropwise over 5 min. and the temperature was kept at 10-12° C. The reaction mixture was stirred at 10° C. for another 10 min, and TLC showed that no starting material left. The reaction mixture was cooled to −30° C. followed by addition of phosphate buffer (200 mL, pH=6.9, 0.5 M) to consume excess reagents. The resulting reaction mixture was stirred in cold room (4° C.) for 48 h. Most of triphenylphosphine was consumed as determined by LCMS. The organic phase was separated and the aqueous phase was extracted by $CH_2$ $Cl_2$ (2×100 mL). Combined organic phase was washed by water (100 mL) and brine (100 mL) and dried over $Na_2SO_4$. All solvent was removed under reduced pressure on a rotary evaporator followed by the addition of ethyl acetate (40 mL) to precipitate triphenylphosphine oxide. After filtering and washing with $CH_2$ $Cl_2$, the filtrate was concentrated. The crude product 12b was purified by flash chromatography eluting with EtOAc/toluene (60/40; column 4×28 cm) to give desired product 12b (3.41 g, 3.92 mmol, 76% yield). $^1$H NMR (400 MHz, $CDCl_3$): consistent with proposed structure for compound 12b. MS: m/z=869.1 (M+1).

Example 13

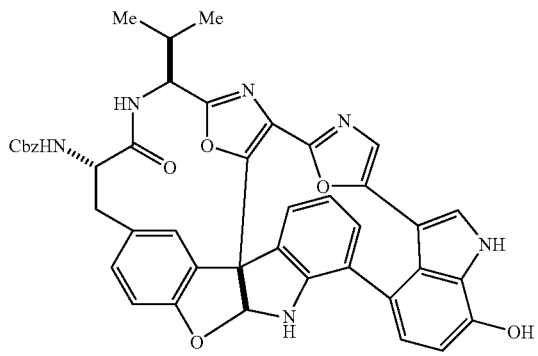

The solution of compound 12b (1.2 g, 1.38 mmol) in acetonitrile (400 mL) was added to a 500-mL flask of a Hanovia photoreactor in a photochemical safety cabinet. The solution was degassed by a stream of argon for 30 min. Then a pre-degassed aqueous solution of lithium hydroxide (83 mg/70 mL, 3.45 mmol, 2.5 eq.) was added by syringe. The resulting solution was degassed again for another 1 h. The door of cabinet was closed. Then the water flow (for cooling the UV lamp) was turned on and UV lamp (with Pyrex filter) was turned on. The reaction solution was irradiated with UV for 120 min followed by quenching with 70 mL of saturated $NH_4$ Cl. The organic phase was separated and the aqueous phase was extracted with ethyl acetate (2×100 mL). The combined organic phase was washed with brine (100 mL) and dried over $Na_2SO_4$. This photoreaction protocol was performed three times using a total of 3.41 g (3.92 mmol) of starting material 12b. All crude product was combined and purified by flash chromatography eluting with an EtOAc-$CH_2$ $Cl_2$ gradient (40:60 to 55:45) to afford desired product 13b (1.29 g, 1.72 mmol, 44% yield). $^1$H NMR (400 MHz, $CDCl_3$): consistent with proposed structure for compound 13b. MS: m/z=747.2 (M+H$^+$). Deacetylated starting material (865 mg, 1.05 mmol, 27% yield) was recovered.

Example 14

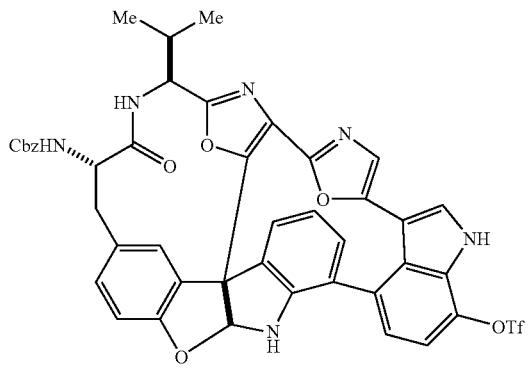

To a dry 250-mL two-neck round-bottom flask equipped with a thermometer containing compound 13b (1.29 g, 1.72 mmol) was added anhydrous CH$_2$Cl$_2$ (100 mL) and TEA (0.719 mL, 5.16 mmol, 3.0 eq.). The suspension was cooled to 0° C. in ice-brine bath followed by addition of the solution of trifluoromethanesulfonic anhydride (0.407 mL, 2.41 mmol, 1.4 eq.) in anhydrous CH$_2$Cl$_2$ (14 mL) dropwise at 0° C. The mixture was stirred at 0° C. under N$_2$ for 2 h and TLC showed that all starting material was consumed. Saturated NaHCO$_3$ (20 mL) was added to quench the reaction. The organic phase was separated, washed by water (30 mL) and brine (2×30 mL) and dried over Na$_2$SO$_4$. The solution was concentrated to afford crude product 14b (1.50 g, 1.71 mmol) which was used directly in next step without further purification. $^1$H NMR (400 MHz, CDCl$_3$): consistent with proposed structure for compound 14b. MS: m/z=879.2 (M+1).

Example 15

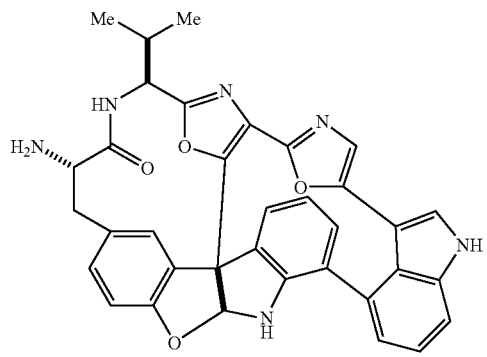

To a 250-mL round-bottom flask containing crude compound 14b (1.47 g, 1.67 mmol) was added methanol (75 mL) and TEA (0.838 mL, 6.0 mmol, 3.6 eq.). The flask was purged with N$_2$ flow for 10 min followed by addition of Pd(OH)$_2$/C (2.64 g, 20%, 3.76 mmol, 2.2 eq.) under N$_2$. H$_2$ balloon was added and the flask was purged with H$_2$ four times. Then hydrogen-filled balloon was opened to the reaction system. After 6.5 h stirring about 5% of starting material remained. The reaction was stopped. The reaction mixture was filtered through a pad of Celite and the black cake was washed with methanol (5×15 mL). The filtrate was concentrated and the residue was dissolved in CH$_2$Cl$_2$ (500 mL). The resulting solution was washed with water (3×100 mL), brine (100 mL), and dried over Na$_2$SO$_4$. The solution was concentrated to afford crude product 15b (930 mg, 1.56 mmol) which was used directly in next step without further purification. $^1$H NMR (400 MHz, CD$_3$OD): consistent with proposed structure for compound 15b. MS: m/z=597.2 (M+1).

Example 16

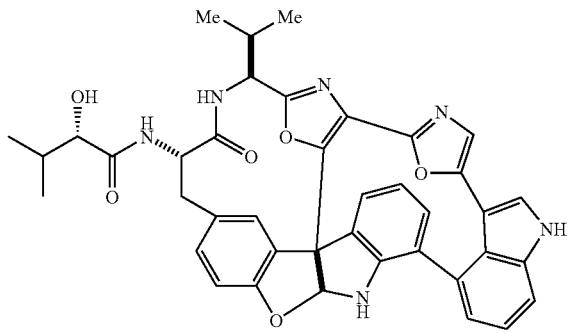

To a dry 100-mL round-bottom flask containing compound 15b (930 mg, 1.56 mmol) was added anhydrous tetrahydrofuran (45 mL). The solution of N-hydroxysuccinimide ester of (S)-2-hydroxy-3-methylbutyric acid (503 mg, 2.34 mmol, 1.5 eq.) in anhydrous tetrahydrofuran (4 mL) was added dropwise at room temperature under N$_2$. The resulting reaction solution was stirred for 18 h. Less than 5% of starting material remained. All solvent was evaporated under reduced pressure and the residue was dissolved in methanol (200 mL). The solution was cooled to 0° C. in ice-water bath followed by the addition of aqueous KOH (1 N, 7 mL) to consume excess reagent. The solution was stirred at 0° C. for 30 min. Then saturated NH$_4$Cl (40 mL) was added at 0° C. to neutralize the base. Most of the methanol was evaporated under reduced pressure and the residue was dissolved in EtOAc (500 mL) followed by washing with saturated NaHCO$_3$ (100 mL), water (2×100 mL) and brine (100 mL) and dried over Na$_2$SO$_4$. The solution was concentrated and the crude was purified by flash chromatography eluting with EtOAc/CH$_2$Cl$_2$ gradient (60/40, 70/30, 80/20 and pure EtOAc) to afford desired product 16b (563 mg, 0.808 mmol, 48% combined yield over three steps from compound 13b). $^1$H NMR (500 MHz, CD$_3$OD): consistent with proposed structure for compound 16b. MS: m/z=697.2 (M+1).

Example 17

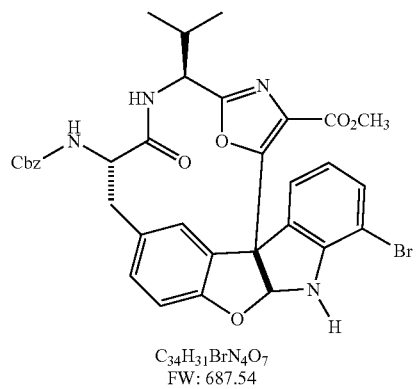

C$_{34}$H$_{31}$BrN$_4$O$_7$
FW: 687.54

An electrochemical cell was assembled using a polyethylene cylinder (15 cm diameter×30 cm height) and a custom rack (polypropylene and nylon) which supported 48 vertical graphite rods (6.15 mm diameter×30 cm length). The rods were arranged in a pattern of three concentric rings with 12 and 24 anodes in the inner and outer rings, respectively. The intermediate ring contained 12 cathodes, separated from adjacent anodes by approximately 7 mm. Electrodes were immersed to a depth of 24 cm. The starting material 7b (20.00 g, 29.0 mmol) and Et$_4$NBF$_4$ (70.00 g, 322 mmol) were dissolved in DMF (4000 mL), and KOH (~86%, 1.68 g, 26 mmol) was added in 10 mL of H$_2$O. The solution was stirred vigorously by two 4-bladed turbines (50 mm diameter, blades at 45°, approx. 680 rpm) on a single shaft. The electrochemical reaction was carried out at a potential of 1.5-1.6 volts. Additional starting material 7 (20.00 g, 20.00 g, 20.00 g, and 7.94 g) was added as a solid, along with KOH (~86%, 1.60 g, 1.63 g, 1.53 g, and 0.65 g) in H$_2$O (5.0 mL, 5.0 mL, 5.0 mL, and 2.0 mL) on days 3, 5, 8, and 10, respectively. After 13 days, approximately 27.7 amp-h of current had passed, and 5.8% of the original starting material remained as determined by HPLC integration at 220 nM. The reaction mixture was concentrated on a rotary evaporator (bath temp. ≦35° C.) and dried further on a vacuum manifold. The residue was partitioned between EtOAc (1200 mL) and 0.5 N aqueous HCl (600 mL). The organic layer was washed with saturated aqueous NaHCO₃ (250 mL) and then saturated aqueous NaCl (250 mL). The aqueous layers were extracted in succession with EtOAc (2×250 mL). The combined organic layers were dried (Na₂SO₄), decanted and evaporated to give the crude product (70.1 g). This material was purified by flash column chromatography in three portions. Each portion used silica gel (283 g) with 25% EtOAc in CH₂Cl₂ (approx. 2.4 L for packing column and elution). This yielded the product (35.6 g, 41% yield) as a mixture of diastereomers (83.5:13.6 as measured by HPLC integration at 220 nm). MTBE (500 mL) was added and the mixture was stirred at room temperature for 2 h. After standing an additional 3 h, the mixture was filtered and the solid was washed with MTBE (3 portions, 100 mL total). HPLC analysis of the filtrate showed 94.8% purity (94.8:2.1 stereoisomer ratio as measured by integration at 220 nm). The filtrate was evaporated and the resulting residue was dried under vacuum to yield product 8b (31.99 g, 36% yield) as a pale yellow solid. ¹H NMR (300 MHz, CDCl₃): consistent with proposed structure for compound 8b. MS: m/z=687.0 (M+1).

Example 18

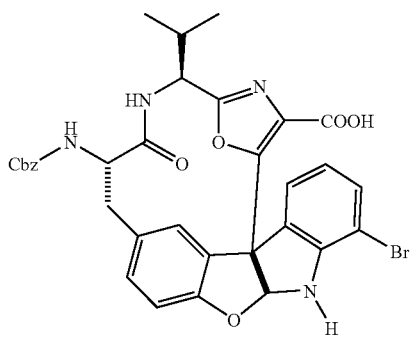

To a three-neck round-bottom flask equipped with a thermometer, an addition funnel and a magnetic stir bar was added the starting methyl ester (530 mg, 0.77 mmol, containing ca. 96% of compound 8b (from Example 17) and methanol (18 mL). The solution was cooled to 0° C. in ice-water bath followed by addition of LiOH in water (324 mg/5 mL, 7.7 mmol, 10 eq.) at 0° C. with stirring. After addition the reaction mixture became a slurry. The cooling bath was removed and the mixture was allowed to warm to room temperature. The precipitate disappeared gradually. After 4.5 h stirring at room temperature less than 2% of starting material remained as determined by LCMS. Ice (40 g) was added to the reaction mixture and HCl/H₂O (1 N, 10 mL) was added dropwise from an addition funnel with vigorous stirring to acidify the 0° C. reaction mixture. The pH of the mixture was adjusted to 2.5-3.0. A pale yellow solid precipitated, which was extracted using ethyl acetate (2×50 mL). The aqueous phase was concentrated to remove most of the methanol and then extracted with ethyl acetate (2×50 mL). The combined organic layers was dried over Na₂SO₄ and concentrated to afford crude product 9b (516 mg, 0.77 mmol, ca. 96% pure and containing by-product hydantoin) which was used directly in the next step without further purification. ¹H NMR (400 MHz, CDCl₃): consistent with proposed structure for compound 9b. MS: m/z=673.2 (M+1).

Example 19

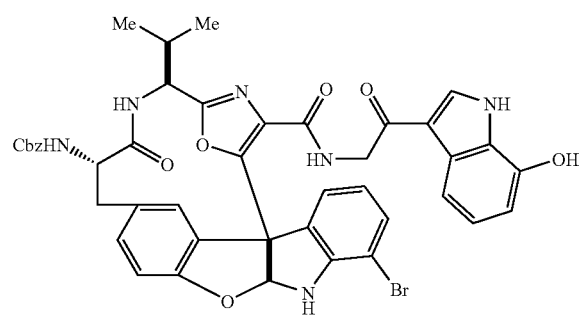

DMF (7 mL) was added to the starting material 9b (157 mg, 0.23 mmol, ca. 96% pure) (from Example 18), HOBt (38 mg, 0.28 mmol, 1.2 eq.), and 2-amino-1-(7-hydroxy-1H-indol-3-yl)ethanone hydrochloride (66 mg, 0.28 mmol, 1.2 eq.) in a round-bottom flask. Diisopropylethylamine (0.051 mL, 37 mg, 0.29 mmol, 1.25 eq.) was added, followed by EDC (49 mg, 0.26 mmol, 1.1 eq.). After stirring for 12 h at 25° C., most of DMF was removed under vacuum. The residue was dissolved in ethyl acetate (100 mL) and washed with 1 N aqueous HCl (50 mL), saturated aqueous sodium bicarbonate (50 mL), and saturated aqueous sodium chloride (50 mL). The solution was dried (Na₂SO₄). After concentration the crude product 10b (186 mg, 0.22 mmol, 94%) was obtained and used directly in next step without further purification. ¹H NMR (400 MHz, CD₃OD): consistent with proposed structure for compound 10b. MS: m/z=845.1 (M+1).

Example 20

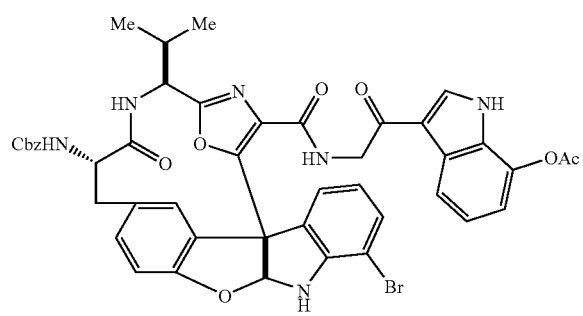

To a dry 50 mL flask containing crude compound 10b (78 mg, 0.09 mmol) (from Example 19) was added anhydrous tetrahydrofuran (0.4 mL) and anhydrous CH₂Cl₂ (1.7 mL). The resulting solution was cooled to 0° C. in ice-water bath. Acetic anhydride (0.027 mL, 0.27 mmol, 3.0 eq.) and pyridine (0.012 mL, 0.14 mmol, 1.5 eq.) were added sequentially at 0° C. Then the mixture was allowed to warm to room temperature and stirred under N₂. The reaction was monitored using LCMS. After 3.5 h only 3% of starting material was not consumed. The reaction solution was diluted with ethyl acetate (40 mL) followed by washing with brine (2×30 mL) and drying over Na₂SO₄. After concentration, the crude product 11b (82 mg, 0.09 mmol, 99% yield) was obtained and used directly in next step without further purification. $^1$H NMR (400 MHz, CDCl$_3$): consistent with proposed structure for compound 11b. MS: m/z=887.2 (M+1).

Example 21

Representative Embodiments of the Invention

The following representative embodiments are intended to illustrate but not to limit the scope of the invention.

A1. A method for the preparation of a compound of formula (I):

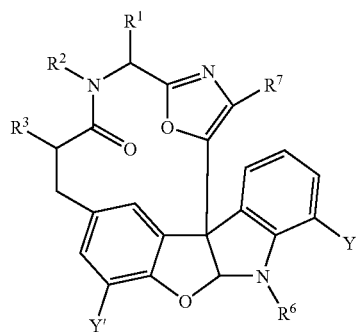

or a salt thereof;
wherein R$^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

R$^2$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; or R$^1$ and R$^2$ may be taken together with the atoms to which they are attached to form a 5- or 6-member ring containing one nitrogen atom;

R$^3$ is H, or —NR$^4$R$^5$;

R$^4$ is H, or C1-C4 alkyl;

R$^5$ is H, or C1-C8 alkyl, C1-C8 heteroalkyl, C6-C14 arylalkyl, C6-C14 heteroarylalkyl, arylsulfonyl, trialkylsilyl, or alkoxycarbonyl, each of which may be optionally substituted; or —C(=X)R' where X is O, S, or NH, and R' is optionally fluorinated C1-C8 alkyl, C2-C8 alkenyl, C5-C12 aryl, or C6-C14 arylalkyl, each of which may be optionally substituted; or R$^4$ and R$^5$ may be taken together with nitrogen to form an imine, or an optionally substituted 3-8 membered monocyclic azacyclic ring or 8-12 membered bicyclic fused azacyclic ring, each of which may contain 0-2 additional heteroatoms selected from N, O, and S as ring members;

R$^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

R$^7$ is H, or halo, —CN, optionally substituted C1-C6 acyl, —COOR$^8$, or —C(O)NR$^9_2$;

R$^8$ is H, or C1-C8 alkyl, C2-C8 alkenyl, C5-C6 aryl, C6-C14 arylalkyl, or trialkylsilyl; and each R$^9$ is independently H, or C1-C8 alkyl, C2-C8 alkenyl, C5-C6 aryl, C6-C14 arylalkyl, C6-C14 heteroarylalkyl, —OH, or C1-C4 alkoxy, each of which may be optionally substituted; or two R$^9$ on the same N can optionally cyclize to form a ring; and each of Y and Y' is independently H, or halo, —OH, or —OR$^{10}$, where R$^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted;

said method comprising electrochemical oxidation of a compound of formula (II):

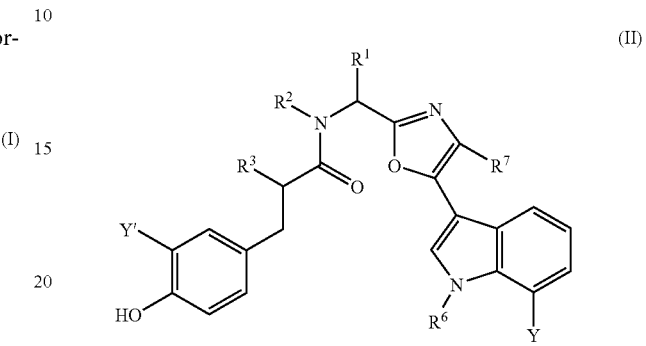

in which the radicals R$^1$, R$^2$, R$^3$, R$^6$, R$^7$, Y, and Y' are as defined for formula (I).

A2. The method according to embodiment A1, wherein the compound of formula (I) having the structure:

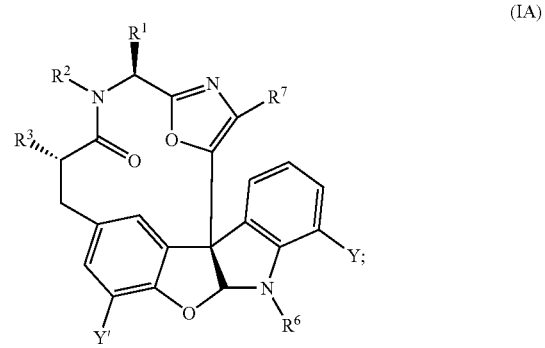

wherein R$^3$ is —NR$^4$R$^5$; and
R$^1$, R$^2$, R$^4$, R$^5$, R$^6$, R$^7$, Y and Y' are defined as for formula (I);

is prepared by electrochemical oxidation of the compound of formula (II) having the structure:

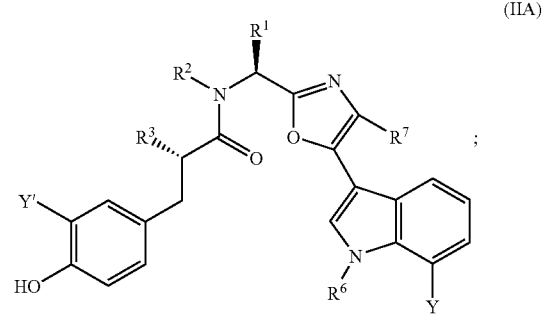

wherein R$^1$, R$^2$, R$^3$, R$^6$, R$^7$, Y and Y' are defined as for formula (IA).

A3. The method according to embodiment A1, wherein the compound of formula (I) having the structure:

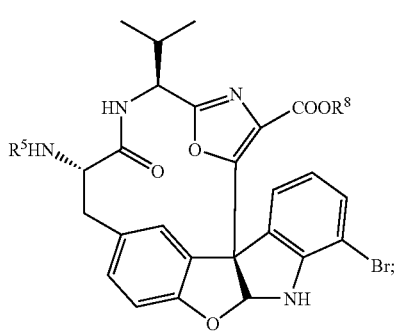

(IB)

wherein $R^5$ is alkoxycarbonyl; and $R^8$ is H, or C1-C8 alkyl, C2-C8 alkenyl, C5-C6 aryl, C6-C14 arylalkyl, or trialkylsilyl;

is prepared by electrochemical oxidation of the compound of formula (II) having the structure:

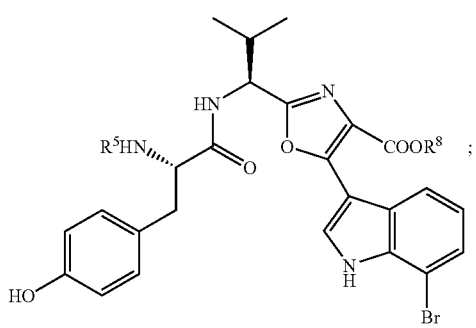

(IIB)

wherein $R^5$ and $R^8$ are defined as for formula (IB).

A4. The method according to embodiment A1, wherein the compound of formula (I) having the structure:

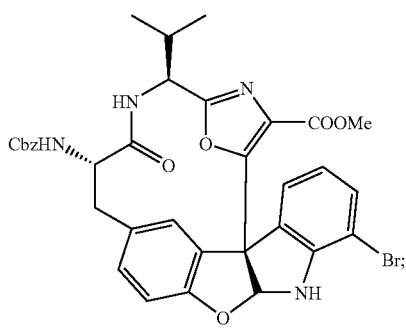

is prepared by electrochemical oxidation of the compound of formula (II) having the structure:

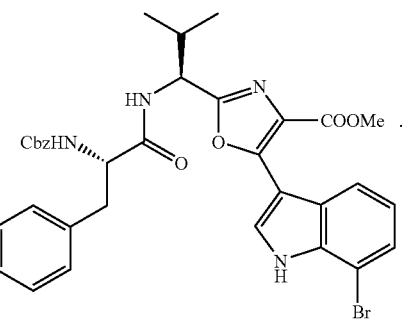

A5. The method according to embodiment A1, wherein the compound of formula (I) having the structure:

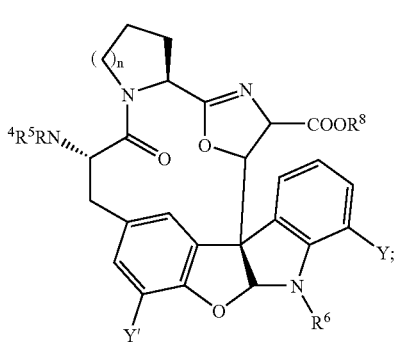

(IC)

is prepared by electrochemical oxidation of the compound of formula:

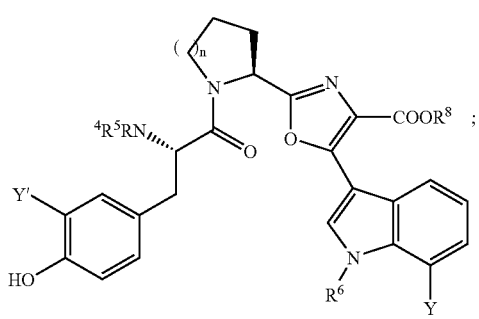

(IIC)

wherein $R^4$, $R^5$, $R^6$, $R^8$, Y and Y' are defined as for formula (I); and n is 1 or 2.

A6. The method according to any one of embodiments A1 to A5, further comprising a purification step, wherein the compound of formula (I) is purified by chromatography, by recrystallization, by trituration, or by a combination of methods.

A7. The method according to any one of embodiments A1 to A6, wherein the purification step comprises:

(i) trituration of the product of formula (I) with MTBE;

(ii) filtration; and (iii) concentration of the filtrate;

to provide the compound of formula (I) in greater than 90% d.e.

A8. The method according to any one of embodiments A1 to A7, wherein the electrochemical oxidization is carried out in an electrolyte that contains a conducting salt.

A9. The method according to any one of the preceding embodiments, wherein the conducting salt is a tetra($C_{1-6}$-alkyl)-ammonium salt comprising at least one counterion selected from the group consisting of sulfate, hydrogensulfate, alkylsulfate, arylsulfate, alkylsulfonate, arylsulfonate, halide, phosphate, carbonate, alkylphosphate, alkylcarbonate, nitrate, alcoholate, tetrafluoroborate and perchlorate.

A10. The method according to any one of the preceding embodiments, wherein the conducting salt is tetraethylammonium tetrafluoroborate.

A11. A method according to any one of the preceding embodiments, wherein the electrochemical oxidation is carried out in an undivided electrolysis cell.

A12. The method according to any one of the preceding embodiments, wherein the electrochemical oxidation is carried out at current densities of from about 5 to about 40 mA/cm$^2$.

A13. The method according to any one of the preceding embodiments, wherein the electrochemical oxidation is carried out at a voltage of from about 1 to about 5 volts.

A14. The method according to any one of the preceding embodiments, wherein the electrochemical oxidation is carried out at a voltage of from about 1.5 to about 1.7 volts.

A15. The method according to any one of the preceding embodiments, wherein the anode comprises carbon or graphite.

A16. The method according to any one of the preceding embodiments, wherein the cathode comprises carbon, graphite, nickel, stainless steel or steel.

A17. The method according to any one of the preceding embodiments, wherein the electrochemical oxidation is carried out from about 0° C. to about 60° C.

A18. The method according to any one of the preceding embodiments, wherein the electrochemical oxidation is carried out from about 10° C. to about 25° C.

A19. The method according to any one of the preceding embodiments, wherein the electrochemical oxidation is carried out in a solvent medium comprising a solvent or a mixture of co-solvents.

A20. The method according to embodiment A19, wherein said solvent medium comprises a solvent selected from the group consisting of DMF, DMA, NMP, sulfolane, pyridine, acetonitrile, a straight or branched chain C1-C4 alcohol, water, ethylene carbonate, propylene carbonate, and mixtures thereof.

A21. The method according to embodiment A19 or A20, wherein the electrochemical oxidation is carried out in a solvent medium comprising at least 50% DMF.

A22. A compound of formula (I):

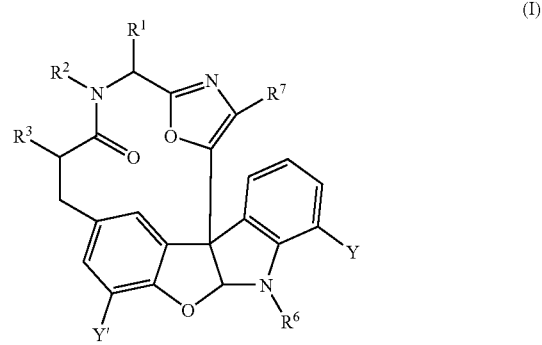

(I)

or a salt thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; or $R^1$ and $R^2$ may be taken together with the atoms to which they are attached to form a 5- or 6-member ring containing one nitrogen atom;

$R^3$ is H, or —NR$^4$R$^5$;

$R^4$ is H, or C1-C4 alkyl;

$R^5$ is H, or C1-C8 alkyl, C1-C8 heteroalkyl, C6-C14 arylalkyl, C6-C14 heteroarylalkyl, arylsulfonyl, trialkylsilyl, or alkoxycarbonyl, each of which may be optionally substituted; or —C(=X)R' where X is O, S, or NH, and R' is optionally fluorinated C1-C8 alkyl, C2-C8 alkenyl, C5-C12 aryl, or C6-C14 arylalkyl, each of which may be optionally substituted; or $R^4$ and $R^5$ may be taken together with nitrogen to form an imine, or an optionally substituted 3-8 membered monocyclic azacyclic ring or 8-12 membered bicyclic fused azacyclic ring, each of which may contain 0-2 additional heteroatoms selected from N, O, and S as ring members;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

$R^7$ is H, or halo, —CN, optionally substituted C1-C6 acyl, —COOR$^8$, or —C(O)NR$^9_2$;

$R^8$ is H, or C1-C8 alkyl, C2-C8 alkenyl, C5-C6 aryl, C6-C14 arylalkyl, or trialkylsilyl; and each $R^9$ is independently H, or C1-C8 alkyl, C2-C8 alkenyl, C5-C6 aryl, C6-C14 arylalkyl, C6-C14 heteroarylalkyl, —OH, or C1-C4 alkoxy, each of which may be optionally substituted; or two $R^9$ on the same N can optionally cyclize to form a ring; and each of Y and Y' is independently H, or halo, —OH, or —OR$^{10}$, where R$^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted.

A23. The compound of formula (I) as in embodiment A22, prepared by the method of any one of embodiments A1 to A21.

A24. A method for the preparation of a compound of formula (3a):

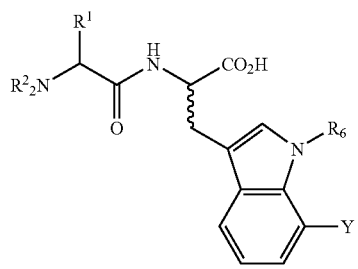

(3a)

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

each $R^2$ is independently H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; and Y is H, or halo, —OH, or —$OR^{10}$, where $R^{10}$ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted;

said method comprising the steps of:

(a) contacting a compound of formula (2a):

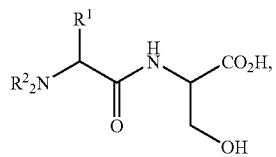

(2a)

with an indole of the formula:

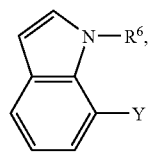

optionally in the presence of a protic acid, to provide a mixture;

wherein $R^1$, $R^2$, $R^6$, and Y are as defined for formula (3a);

(b) adding an activating reagent to said mixture; and (c) optionally heating said mixture to provide the compound of formula (3a).

A25. The method according to embodiment A24, comprising the steps of:

(a) contacting the compound of formula (2a) with the indole in a protic acid which is acetic acid, to provide a mixture;

(b) adding an activating reagent which is acetic anhydride to said mixture; and (c) heating said mixture at about 80° C. to provide the compound of formula (3a).

The invention claimed is:

1. A method for the preparation of a compound of formula (I):

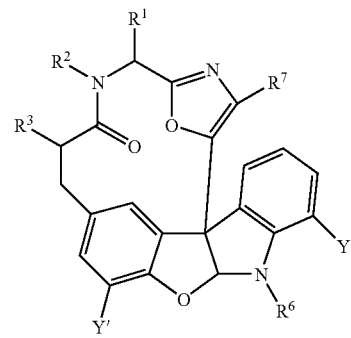

(I)

or a salt thereof;

wherein $R^1$ is H, or C1-C8 alkyl, C2-C8 alkenyl, C2-C8 alkynyl, C5-C6 aryl, C6-C12 arylalkyl, or a heteroform of one of these, each of which may be optionally substituted;

$R^2$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted; or $R^1$ and $R^2$ may be taken together with the atoms to which they are attached to form a 5- or 6-member ring containing one nitrogen atom;

$R^3$ is H, or —$NR^4R^5$;

$R^4$ is H, or C1-C4 alkyl;

$R^5$ is H, or C1-C8 alkyl, C1-C8 heteroalkyl, C6-C14 arylalkyl, C6-C14 heteroarylalkyl, arylsulfonyl, trialkylsilyl, or alkoxycarbonyl, each of which may be optionally substituted; or —C(=X)R' where X is O, S, or NH, and R' is optionally fluorinated C1-C8 alkyl, C2-C8 alkenyl, C5-C12 aryl, or C6-C14 arylalkyl, each of which may be optionally substituted; or $R^4$ and $R^5$ may be taken together with nitrogen to form an imine, or an optionally substituted 3-8 membered monocyclic azacyclic ring or 8-12 membered bicyclic fused azacyclic ring, each of which may contain 0-2 additional heteroatoms selected from N, O, and S as ring members;

$R^6$ is H, or C1-C8 alkyl, C1-C8 heteroalkyl, C6-C14 arylalkyl, C6-C14 heteroarylalkyl, optionally fluorinated C1-C6 acyl, C6-C12 aroyl, arylsulfonyl, trialkylsilyl, or alkoxycarbonyl, each of which may be optionally substituted;

$R^7$ is H, or halo, —CN, optionally substituted C1-C6 acyl, —$COOR^8$, or —$C(O)NR^9_2$;

$R^8$ is H, or C1-C8 alkyl, C2-C8 alkenyl, C5-C6 aryl, C6-C14 arylalkyl, or trialkylsilyl; and each $R^9$ is independently H, or C1-C8 alkyl, C2-C8 alkenyl, C5-C6 aryl, C6-C14 arylalkyl, C6-C14 heteroarylalkyl, —OH, or C1-C4 alkoxy, each of which may be optionally substituted; or two R⁹ on the same N can optionally cyclize to form a ring; and each of Y and Y' is independently H, or halo, —OH, or —OR¹⁰, where R¹⁰ is optionally fluorinated C1-C4 alkyl, C2-C4 alkenyl, C6-C14 arylalkyl, optionally fluorinated alkylsulfonyl, arylsulfonyl, optionally fluorinated C1-C6 acyl, or C6-C10 aroyl, each of which may be optionally substituted;

said method comprising electrochemical oxidation of a compound of formula (II):

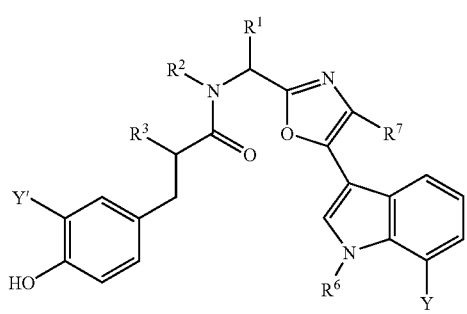

(II)

in which the radicals $R^1$, $R^2$, $R^3$, $R^6$, $R^7$, Y, and Y' are as defined for formula (I).

2. The method according to claim 1, wherein the compound of formula (I) having the structure:

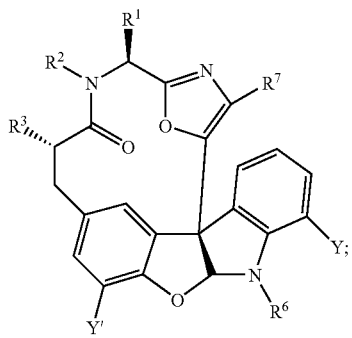

(IA)

wherein $R^3$ is —NR⁴R⁵; and $R^1$, $R^2$, $R^4$, $R^5$, $R^6$, $R^7$, Y and Y' are defined as for formula (I);

is prepared by electrochemical oxidation of the compound of formula (II) having the structure:

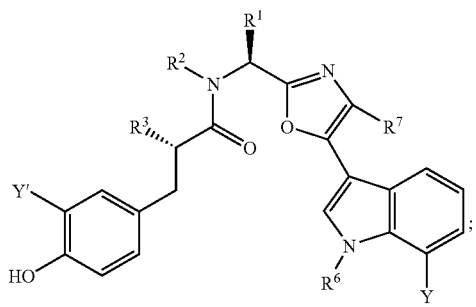

(IIA)

wherein $R^1$, $R^2$, $R^3$, $R^6$, $R^7$, Y and Y' are defined as for formula (IA).

3. The method according to claim 1, wherein the compound of formula (I) having the structure:

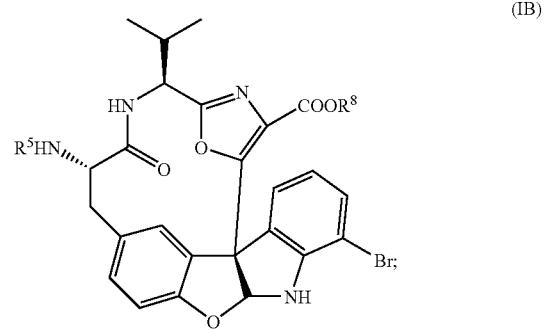

(IB)

wherein R⁵ is alkoxycarbonyl; and

R⁸ is H, or C1-C8 alkyl, C2-C8 alkenyl, C5-C6 aryl, C6-C14 arylalkyl, or trialkylsilyl;

is prepared by electrochemical oxidation of the compound of formula (II) having the structure:

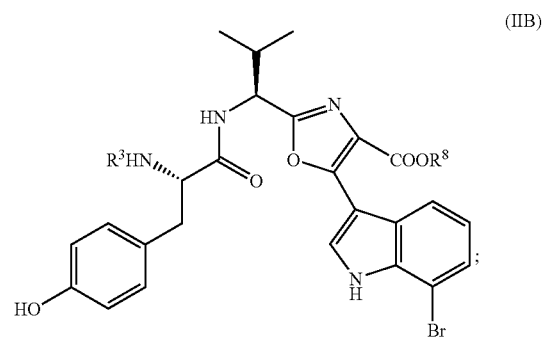

(IIB)

wherein R⁵ and R⁸ are defined as for formula (IB).

4. The method according to claim 1, wherein the compound of formula (I) having the structure:

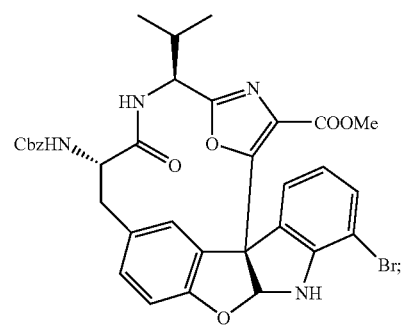

is prepared by electrochemical oxidation of the compound of formula (II) having the structure:

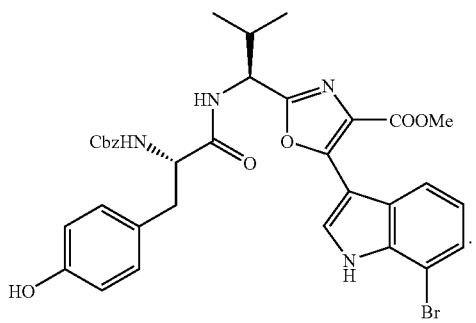

5. The method according to claim 1, wherein the compound of formula (I) having the structure:

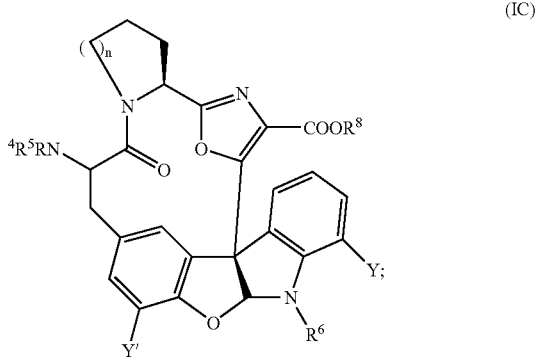

is prepared by electrochemical oxidation of the compound of formula:

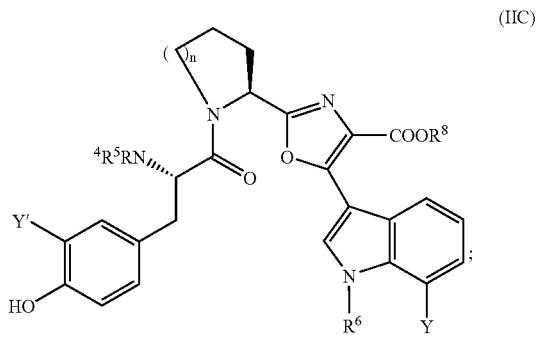

wherein $R^4$, $R^5$, $R^6$, $R^8$, Y and Y' are defined as for formula (I); and n is 1 or 2.

6. The method according to claim 1, further comprising a purification step, wherein the compound of formula (I) is purified by chromatography, by recrystallization, by trituration, or by a combination of methods.

7. The method according to claim 6, wherein the purification step comprises:
   (i) trituration of the product of formula (I) with MTBE;
   (ii) filtration; and
   (iii) concentration of the filtrate;
   to provide the compound of formula (I) in greater than 90% d.e.

8. The method according to claim 1, wherein the electrochemical oxidization is carried out in an electrolyte that contains a conducting salt.

9. The method according to claim 8, wherein the conducting salt is a tetra($C_{1-6}$-alkyl)-ammonium salt comprising at least one counterion selected from the group consisting of sulfate, hydrogensulfate, alkylsulfate, arylsulfate, alkylsulfonate, arylsulfonate, halide, phosphate, carbonate, alkylphosphate, alkylcarbonate, nitrate, alcoholate, tetrafluoroborate and perchlorate.

10. The method according to claim 9, wherein the conducting salt is tetraethylammonium tetrafluoroborate.

11. A method according to claim 1, wherein the electrochemical oxidation is carried out in an undivided electrolysis cell.

12. The method according to claim 1, wherein the electrochemical oxidation is carried out at current densities of from about 5 to about 40 mA/cm$^2$.

13. The method according to claim 1, wherein the electrochemical oxidation is carried out at a voltage of from about 1 to about 5 volts.

14. The method according to claim 1, wherein the electrochemical oxidation is carried out at a voltage of from about 1.5 to about 1.7 volts.

15. The method according to claim 1, wherein the anode comprises carbon or graphite.

16. The method according to claim 1, wherein the cathode comprises carbon, graphite, nickel, stainless steel or steel.

17. The method according to claim 1, wherein the electrochemical oxidation is carried out from about 0° C. to about 60° C.

18. The method according to claim 1, wherein the electrochemical oxidation is carried out from about 10° C. to about 25° C.

19. The method according to claim 1, wherein the electrochemical oxidation is carried out in a solvent medium comprising a solvent or a mixture of co-solvents.

20. The method according to claim 19, wherein said solvent medium comprises a solvent selected from the group consisting of DMF, DMA, NMP, sulfolane, pyridine, acetonitrile, a straight or branched chain C1-C4 alcohol, water, ethylene carbonate, propylene carbonate, and mixtures thereof.

21. The method according to claim 19, wherein the electrochemical oxidation is carried out in a solvent medium comprising at least 50% DMF.

22. The method of claim 1, further comprising a step of converting the compound of formula (I) to a diazonamide analog, wherein the diazonamide analog has a formula selected from the group consisting of:

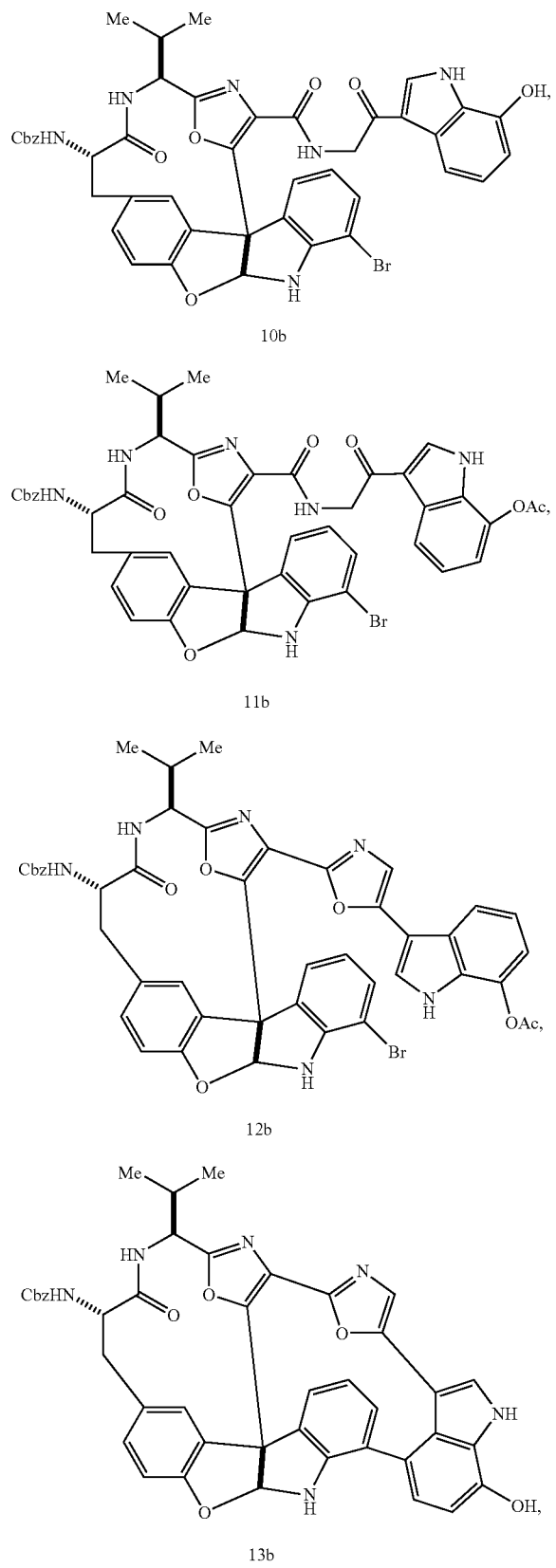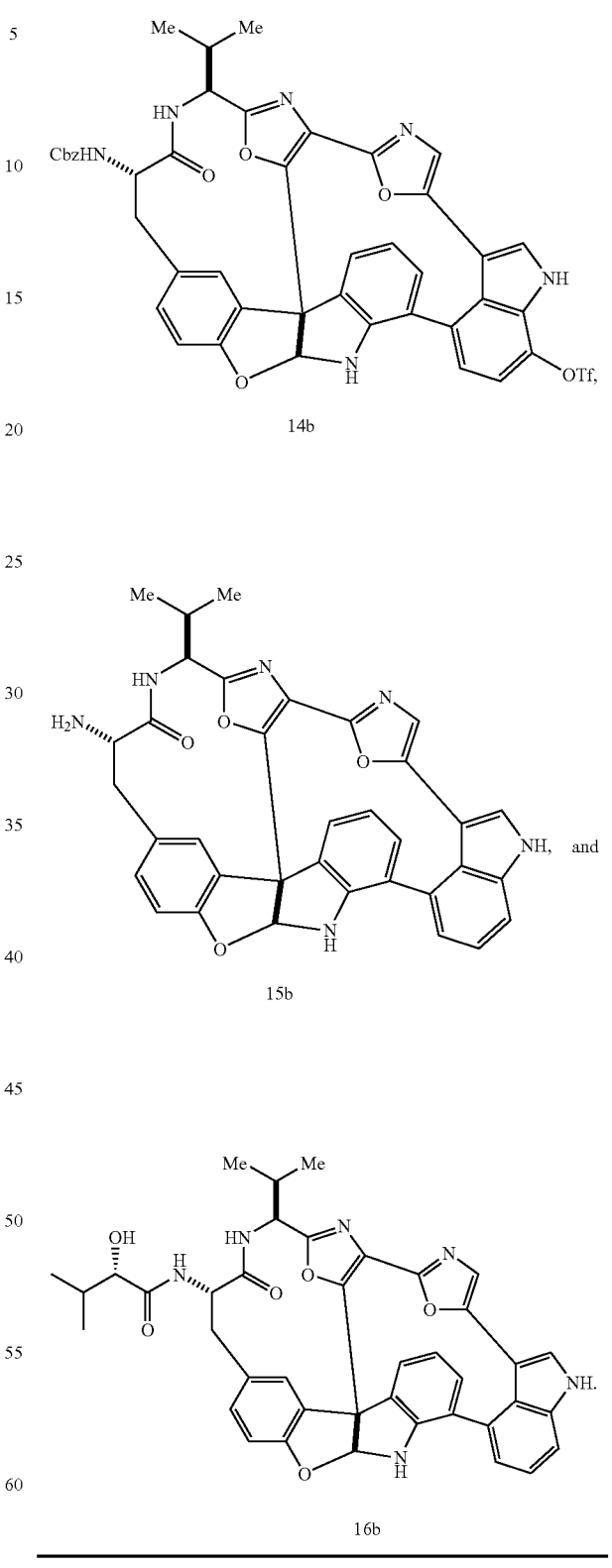
* * * * *

UNITED STATES PATENT AND TRADEMARK OFFICE
CERTIFICATE OF CORRECTION

PATENT NO. : 7,851,620 B2
APPLICATION NO. : 12/134984
DATED : December 14, 2010
INVENTOR(S) : Gunnar Hanson et al.

Page 1 of 1

It is certified that error appears in the above-identified patent and that said Letters Patent is hereby corrected as shown below:

In the Specification

At Column 1, Lines 15-17, the acknowledgement of government funding should read:
--This invention was made with government support under grant number GM060591 awarded by The National Institutes of Health. The government has certain rights in the invention.--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*